United States Patent [19]
John

[11] Patent Number: 5,608,148
[45] Date of Patent: Mar. 4, 1997

[54] TRANSGENIC COTTON PLANTS PRODUCING HETEROLOGOUS PEROXIDASE

[75] Inventor: Maliyakal E. John, Middleton, Wis.

[73] Assignee: Agracetus, Inc., Middleton, Wis.

[21] Appl. No.: 378,588

[22] Filed: Jan. 25, 1995

Related U.S. Application Data

[63] Continuation-in-part of Ser. No. 130,086, Sep. 30, 1993, abandoned.
[51] Int. Cl.$^6$ .............................. A01H 1/04; C12N 5/14; C12N 15/00
[52] U.S. Cl. .................. 800/205; 800/255; 800/DIG. 27; 435/172.3; 435/419
[58] Field of Search .......................... 800/205, DIG. 27, 800/255; 435/172.1, 172.3, 240.5, 240.49; 536/24.1, 23.1; 935/6, 35, 67

[56] References Cited

PUBLICATIONS

Rao et al (1982) Z. Pflanzenphysiol Bd. 106 S. 157–165.
Finer et al (1990) Plant Cell Reports 8:586–589.
Thaker et al (1986) J Plant Growth Regul 5:17–27.
John et al (1989) J Cell Biochem Suppl 13D, p. 280 Abstract M221.
Josefsson et al (1987) J Biol Chem 262 (25) pp. 12196–12201.
Lagrimini et al (1987) Proc. Natl. Acad Sci 84:7542–7546.
Poehlman (1959) 'Breeding Cotton' in *Breeding Field Crops* pp. 305–327, Holt Rinehardt and Winston Inc, NY.
Black and Reddy, "Cloning and Characterization of a Lignin Peroxidase Gene from the White–Rot Fungus," *Biochem. Biophys. Research Communications*, 179:428–435 (1991).
Botella, et al., "Nucleotide Sequences of Two Peroxidase Genes from Tomato (*Lycopersicon esculentum*)," *Plant Physiol.* 103:665–666 (1993).
Diaz–De–Leon, et al., "Nucleotide sequence of the Tobacco (*Nicotiana tabacum*) Anionic Peroxidase gene," *Plant Physiol.*, 101:1117–1118 (1993).
Fry, S. C., "Cross–Linking of Matrix Polymers in the Growing Cell Walls of Angiosperms," *Ann. Rev. Plant. Physiol.*, 37:165–186 (1986).
Fujiyama, K., et al., "Structure of the Horseradish Peroxidase Isozyme C Genes," *Eur. J. Biochem.*, 173:681–687 (1988).
Goff, C. W., "A Light and Electron Microscopic Study of Peroxidase Localization in the Onion Root Tip," *Amer. J. Bot.*, 62:280–291 (1975).
Hughes, D. W., and G. A. Galau, "Temporally Modular Gene Expression During Cotyledon Development," *Genes and Dev.*, 3:358–369 (1989).

Intapruk, et al., "Nucleotide Sequences of Two Genomic DNAs Encoding Peroxidase of *Arabidopsis thaliana*," *Gene* 98:237–241 (1991).
Intapruk, C., et al., "Cloning of CDNAs Encoding Two Peroxidases of *Arabidopsis thaliana* and Their Organ–Specific Expression," *J. Ferment. Bioeng.*, 75:166–172 (1993).
Intapruk, C., et al., "Nucleotide Sequences of a New CDNA for Peroxidase from *Arabidopsis thaliana*," *Plant Physiol.*, 10–4:285–286 (1994).
John, M. E., "Genetic Engineering of Cotton for Fiber Modification," In *Proceedings of the Conference on Cotton Fiber Cellulose: Structure, Function, and Utilization*. Natl. Cotton Council, Memphis, TN 91–107 (1992).
John, M. E., "Gene Expression in Cotton (*Gossypium hirsutum*) fiber," in *Proceedings of the International Conference on Biotechnology in Agriculture and Forestry*, Indian Society of Agricultural Biochemists, Feb. 15–18, 1993.
John, M. E., "Potential for Value–Added Fibers from Biotechnology," In *Proceedings of the International Conference on Biotechnology in Agriculture and Forestry*, Indian Society of Agricultural Biochemists, Feb. 15–18 (1993).
John, M. E., "Novel Products from an emerging Technology," In *Cotton International* 60th Edition, 86:88 (1993).
John, M. E., and J. M. Stewart, "Genes for Jeans: Biotechnological Advances in Cotton," *Trends in Biotechnology*, 10:165–170 (1992).
John, et al., *J. Cell Biochem. Suppl.* 13D, p. 280, Abstract M221 (1989).
John, et al., "Characterization of Genes Coding for Fiber Specific mRNAs in Cotton (*Gossypium hirsutum* L.)," Abstract, *Journal of Cellular Biochemistry*, Mar. 27–Apr. 7, 1989.
John, M. E., et al., "Gene Expression in cotton (*Gossypium hirsutum* L.) fiber: Cloning of MRNAS," *Proc. Natl. Acad. Sci.*, 89:5769–5773 (1992).
Johnson, G. W., et al., "Quality Improvements of Cotton Fiber Through Genetic Engineering: Potentials and Problems." Abstract, p. 637 in 1989 *Proceedings of Beltwide Cotton Production Research Conferences*, Nashville, TN (1989).

(List continued on next page.)

*Primary Examiner*—Douglas W. Robinson
*Assistant Examiner*—Elizabeth F. McElwain
*Attorney, Agent, or Firm*—Quarles & Brady

[57] ABSTRACT

A fiber-producing plant comprising in its genome a heterologous genetic construct is disclosed. This genetic construct comprises a fiber-specific promoter and a coding sequence encoding a plant peroxidase. Preferably, the coding sequence is for cotton peroxidase. Seeds of the plant containing this genetic construct and plant cells containing this construct are also disclosed.

9 Claims, 17 Drawing Sheets

PUBLICATIONS

Josefsson, et al., "Structure of a Gene encoding the 1.7S Storage Protein, Napin, from *Brassica napus*," *J. Biol. Chem.*, 262:12196–12201 (1987).

Kawai, et al., "Nucleotide Sequence for the Genomic DNA Encoding an Anionic Peroxidase Gene from a Hybrid Poplar, *Populus kitakamiensis*," *Biosc. Biotech. Biochem.*, 57:131–133 (1993).

Kay and Basile, "Specific Peroxidase Isoenzymes Are Correlated with Organogenesis," *Plant Physiol.*, 84:99–105 (1987).

Klausner, "Researchers Cotton to new Fiber Findings," *Bio–Technology* 3:1049–1051 (1985).

Lagrimini et al., "Molecular Cloning of Complementary DNA Encoding the Lignin–Forming Peroxidase from Tobacco: Molecular Analysis and Tissue–Specific Expression," *Proc. Natl. Acad. Sci. USA*, 84:7542–7546 (1987).

Lagrimini, et al., "Peroxidase–Induced Wilting in Transgenic Tobacco Plants," *The Plant Cell*, 2:7–18 (1990).

Lee, T. T., "Interaction of Cytokinin, Auxin, and Gibberellin on Peroxidase Isoenzymes in Tobacco Tissue Cultured in Vitro," *Can. J. Bot.*, pp. 2471–2477 (1972).

McCabe, D., and B. Martinell, *Biotechnology* 11:596–598 (1993).

McKnight, S. L., et al., "Analysis of Transcriptional Regulatory Signals of the HSV Thymidine Kinase Gene: Identification of an Upstream Control Region," *Cell* 25:385–398 (1981).

Mellon, J. E., "Some Characteristics of Peroxidase Secreted by Cotton Ovule Cultures," *Plant Cell Reports*, 5:338–341 (1986).

Mellon and Triplett, "De Novo Synthesis of Peroxidase in Cotton Ovule Culture Medium," *Physiologia Plantarum*, 77:302–307 (1989).

Morgens, et al., "Isolation and Sequencing of CDNA Clones Encoding Ethylene–Induced Putative Peroxidases from Cucumber Cotyledons," *Plant. Mol. Biol.*, 14:715–725 (1990).

Petersen et al., "Study of Fiber Synthesis Related Genes in Fiber Producing and Non–fiber Producing Species of the Genus *Gossypium*," *Agronomy*, Abstract, Oct. 1988.

Poehlman, "Breeding Corn," pp. 305–327 In *Breeding Field Crops*, Holt–Rinehardt and Winston, Inc., New York.

Rao, et al., "Changes in Indoleacetic Acid Oxidase and Peroxidase Activities During Cotton Fibre Development," *Z. Pflanzenphysiol. Bd.*, 106:157–165 (1982).

Ridge and Osborne, "Hydoxyproline and Peroxidases in Cell Walls of *Pisum sativum*: Regulation by Ethylene," *J. Exp. Botany*, 21:843–856 (1970).

Ritch and Gold, "Characterization of a Highly Expressed Lignin Peroxidase–Encoding Gene from the Basidiomycete *Phanerochaete chrysosporium*," *Gene*, 118:73–80 (1992).

Ritter, et al., "Cotton Cotyledon CDNA Encoding a Peroxidase," *Plant Physiol.*, 102:1351 (1993).

Roberts and Kolattukudy, "Molecular Cloning, Nucleotide Sequence, and Abscisic Acid Induction of a Suberization-–Associated Highly Anionic Peroxidase," *Mol. Gen. Genet.*, 217:223–232 (1989).

Roberts et al., "Cloning and Sequencing of cDNA for a Highly Anionic Peroxidase from Potato and the Induction of its mRNA in suberizing Potato Tubers and Tomato Fruits," *Plant Mol. Biol.*, 11:15–26 (1988).

Sakajo, et al., "Molecular Cloning and Nucleotide Sequence of Full–Length cDNA for Sweet Potato Catalase mRNA," *Eur. J. Biochem.*, 165:437–442 (1987).

Stewart, J. M., and M. E. John, "The Next Promise of Biotechnology," *Cotton Growers*, vol. 29 1:42–43 (1993).

Thaker, et al., "Role of Peroxidase and Esterase Activities During Cotton Fiber Development," *J. Plant Growth Regul.*, 5:17–27 (1986).

Van Fleet, D. S., "The Distribution of Peroxidase in Differentiating Tissues of Vascular Plants," *Biodynamica* 113:125–140 (1947).

Van Huystee, R. B., "Some Molecular Aspects of Plant Peroxidase Biosynthetic Studies," *Ann. Rev. Plant Physiol.*, 38:205–219 (1987).

Venere, R. J., "Role of Peroxidase in Cotton Resistant to Bacterial Blight," *Plant Science Letters*, 20:47–56 (1980).

Whitmore, F. W., "Lignin–Protein Complex Catalyzed by Peroxidase," *Plant Science Letters*, 18:241–245 (1978).

Wilkes–Douglas, et al., "The Application of Recombinant DNA Technology toward Crop Improvement," *Physiol. Planatarum*, 68:560–565 (1986).

Zhou, et al., "Introduction of Exogenous DNA Into Cotton Embryos," *Methods in Enz.*, 101:433–443 (1981).

E6-3B/Nos (A) Fragments

TRANSGENIC COTTON PLANTS PRODUCING HETEROLOGOUS PEROXIDASE

This is a continuation-in-part of application Ser. No. 08/130,086 filed Sep. 30, 1993, now abandoned.

FIELD OF THE INVENTION

The present invention relates to the field of plant genetic engineering. In particular, the present invention relates to the creation of transgenic cotton plants containing a heterologous peroxidase.

BACKGROUND

Peroxidase

Peroxidases are an ubiquitous family of enzymes found in many living organisms, including plants. Many peroxidases are glycoproteins with a heme group located at the active site that oxidize molecules at the expense of hydrogen peroxide. The median molecular weight of these proteins is in the range of 40 to 50 kDa and numerous isoenzymes are known to exist in a given organism.

Peroxidases can be generally divided into anionic, cationic and neutral enzymes. The basis of this distinction is their isoelectric points and probable functions. Cationic isoenzymes (pI 8–11) in the central vacuole catalyze the synthesis of $H_2O_2$ from NADH and $H_2O$ and act as an indole acetic acid oxidase. Neutral isoenzymes (pI 4.6–6.5) on cell walls have activity with lignin precursors and possibly function in wound healing. Strongly anionic (pI 3.5–4) peroxidases function in lignification.

The plant peroxidase isoenzymes may have roles in a wide variety of functions in physiology and development. These roles include auxin catabolism, cross-linking of phenolic components of the cell wall, and suberin and lignin biosynthesis (Gaspar, et al., *Peroxidases 1970–1980: A Survey of their Biochemical and Physiological Roles in Higher Plants*. University of Geneva, Switzerland, pp. 1–324, 1982; Fry, *Ann. Rev. Plant. Physiol.*, 37:165–186, 1986; Mohan and Kolattukudy, *Plant Physiol.*, 92:276–280, 1990; Gross, *Adv. Bot. Res.* 8, 26–65, 1980). Peroxidases are induced by wounding and are presumably involved in the repair and formation of cell walls. Peroxidase has been shown to catalyze the polymerization of phenolic compounds into lignin and form cross-links between extensin, a hydroxyproline rich cell wall protein and lignin, and feruloylated polysacchrides (Reviewed by Grisebach, *The Biochemistry of Plants*, 7:457–478, 1981). They have been also implicated in the regulation of cell wall elongation (Goldberg, et al., in *Molecular and Physiological Aspects of Plant Peroxidases*, Geneva, Switzerland: University of Geneva, pp. 209–220, 1986).

In cotton, peroxidase is located in ovary walls that becomes the carpel tissue of the boll. Peroxidase is also associated with developing ovules and fibers (Mellon, *Plant Cell Rep.*, 5:338–341, 1986; Wise and Morrison, *Pytochemistry*, 10:2355–2359, 1971).

Genetic Engineering of Cotton

Although successful transformation and regeneration techniques have been demonstrated in model plants species such as tobacco (Barton, et al., *Cell.*, 32:1033–1043, 1983), similar results with cotton have only been achieved relatively recently. See, e.g. Umbeck, et al. *Bio/Technology*, 5[3] 263–266 (1987); Firoozabady, et al., *Plant Mol. Bio.*, 10:105–116 (1987); Finer and McMullen., *Plant Cell Rep.*, 8:586–589, 1990. McCabe and Martinell *Bio/Technology*, 11:596–598, 1993.

Cotton is one of the most important cash crops. Successful transformation and regeneration of genetically engineered cotton plants has the potential to be of significant value to this agriculturally important crop. One of the most important benefits potentially achievable from genetically engineering cotton plants is the alteration and modification of cotton fiber quantity and quality.

Cotton fiber (seed hair) is a differentiated single epidermal cell of the ovule. At maturity the fiber cell consists of a cell lumen, primary cell-wall and secondary cell-wall. The primary cell-wall is made up of pectic compounds, cellulose, and small amounts of protein. The secondary cell-wall consists of cellulose. At maturity, the cotton fiber contains 87% cellulose.

Cotton fiber development can be divided into initiation, primary cell-wall synthesis stage, secondary cell-wall deposition stage, and maturation phases. Many hundreds of genes are required for the differentiation and development of cotton fiber. Work on in vitro translated fiber proteins (Delmer, et al., *J. Cell Sci.*, 2:33–50, 1985) and protein isolated from fiber (Graves and Stewart, *J. Exp. Bot.*, 39:59–69, 1988) clearly suggests differential gene expression during various developmental stages of the cell. Only a few of the genes involved in the biosynthesis of the large numbers of fiber-specific structural proteins, enzymes, polysaccharides, waxes or lignins have been identified (John and Crow, *Proc. Natl. Acad. Sci. USA*, 89:5769–5773, 1992). Since these genes and their interactions with environment determine the quality of fiber, their identification and characterization is considered to be an important aspect of cotton crop improvement.

The quality of the cotton fiber is dependent on such factors as the extent of elongation and degree of secondary wall deposition. It is assumed that both a number of genes and environmental factors regulate the physical characteristics of the fiber such as length, strength and micronaire value. However, the genes responsible for cellulose synthesis and fiber development in cotton plants are heretofore entirely uncharacterized at a molecular level.

The most commercially useful plant fiber is derived from cotton (*Gossypium arboreum, Gossypium herbaceum, Gossypium barbadense* and *Gossypium hirsutum*). However, there are other fiber-producing plants with potential commercial uses. These plants include the silk cotton tree (Kapok, *Ceiba pentandra*), desert willow, creosote bush, winterfat, balsa, ramie, kenaf, hemp, roselle, jute, sisal abaca and flax.

Promoters

Promoters are DNA elements that direct the transcription of RNA from DNA sequences. Together with other regulatory elements that specify tissue and temporal specificity of gene expression, promoters control the development of organisms. Thus, there has been a concerted effort in identifying and isolating promoters from a wide variety of plants and animals.

Many promoters function properly in heterologous systems. For example, promoters taken from plant genes such as rbcS, Cab, chalcone synthase and protease inhibitor from tobacco and *Arabidopsis* are functional in heterologous transgenic plants. (Reviewed by Benfey and Chua, *Science*, 244:174–181, 1989). Specific examples of transgenic plants include tissue-specific and developmentally regulated expression of soybean 7s seed storage protein gene in transgenic tobacco plants (Chen, et al. *EMBO J.*, 7:297–302, 1988.) and light-dependent organ-specific expression of

*Arabidopsis thaliana* chlorophyll a/b binding protein gene promoter in transgenic tobacco (Ha and An, *Proc. Natl. Acad. Sci. USA*, 85:8017–8021, 1988). Similarly, anaerobically inducible maize sucrose synthase-1 promoter activity was demonstrated in transgenic tobacco (Yang and Russell, *Proc. Natl. Acad. Sci. USA*, 87:4144–4148, 1990). Tomato pollen promoters were found to direct tissue-specific and developmentally regulated gene expression in transgenic *Arabidopsis* and tobacco (Twell, et al., *Development*, 109:705–714, 1990). Similarly, one cotton promoter has been shown to express a transgene in a fiber-specific manner (John and Crow, *Proc. Natl. Acad. Sci. USA*, 89:5769–5773, 1992). Thus, some plant promoters can be utilized to express foreign proteins in specific tissues in a developmentally regulated fashion.

Many of the features of over-expression of peroxidases could be advantageously combined with plant fiber. Because of the potential for debilitating effects on normal plant physiology by over-production of highly catalytic enzymes such as peroxidase, we believe that it is preferable to confine expression of these enzymes to limited tissues. This strategy allows for normal plant growth and the specific effect of over-expression of the gene in specific tissue, such as fiber. However, a fiber-producing plant containing a tissue-specific peroxidase genetic construct has neither been proposed nor created. What is needed in the art of molecular biology is a plant fiber containing over-expression of peroxidase.

SUMMARY OF THE INVENTION

The present invention is a fiber-producing plant comprising in its genome a genetic construct. This construct comprises a cotton fiber-specific promoter operably linked to a sequence encoding a peroxidase. The peroxidase is expressed in the fiber-producing plant.

Preferably, the peroxidase is expressed at a level equal to or greater than five-fold the native peroxidase level.

Preferably, the sequence encodes plant peroxidase. Most preferably, the sequence encodes cotton peroxidase.

Also preferably, the construct contains a marker gene.

The present invention is also a fiber-producing plant cell comprising the genetic construct described above.

An object of the present invention is to create a fiber-producing plant with altered fiber.

Another object of the present invention is to create a fiber-producing plant with stronger fiber.

Another object of the present invention is to create a fiber-producing plant with excess peroxidase molecules combined with cotton fiber.

It is an advantage of the present invention that the peroxidase genes are over-expressed in fiber and not in other plant tissues where it would be harmful to the plant.

It is another advantage of the present invention that fiber with altered strength is created.

Other objects, advantages, and features of the present invention will become apparent upon examination of the specification and claims.

DESCRIPTION OF THE DRAWINGS

FIG. 4A is a diagram of a clone prepared by excising the E6-3B 3'-end and NOS poly(A) region as a single fragment from pSKSIE6-3B and cloning into the NotI site of the SK⁺ vector. FIG. 4B was prepared by PCR amplification using primers SEQ ID NOs:11 and 12. FIG. 4C was prepared by amplifying a DNA fragment containing the E6-3B 3'-end from clone pSKSIE6-3B, cloning the fragment into the SK⁺ vector and separately adding the NOS poly(A) fragment.

DESCRIPTION OF THE PREFERRED EMBODIMENT

Figure 1:
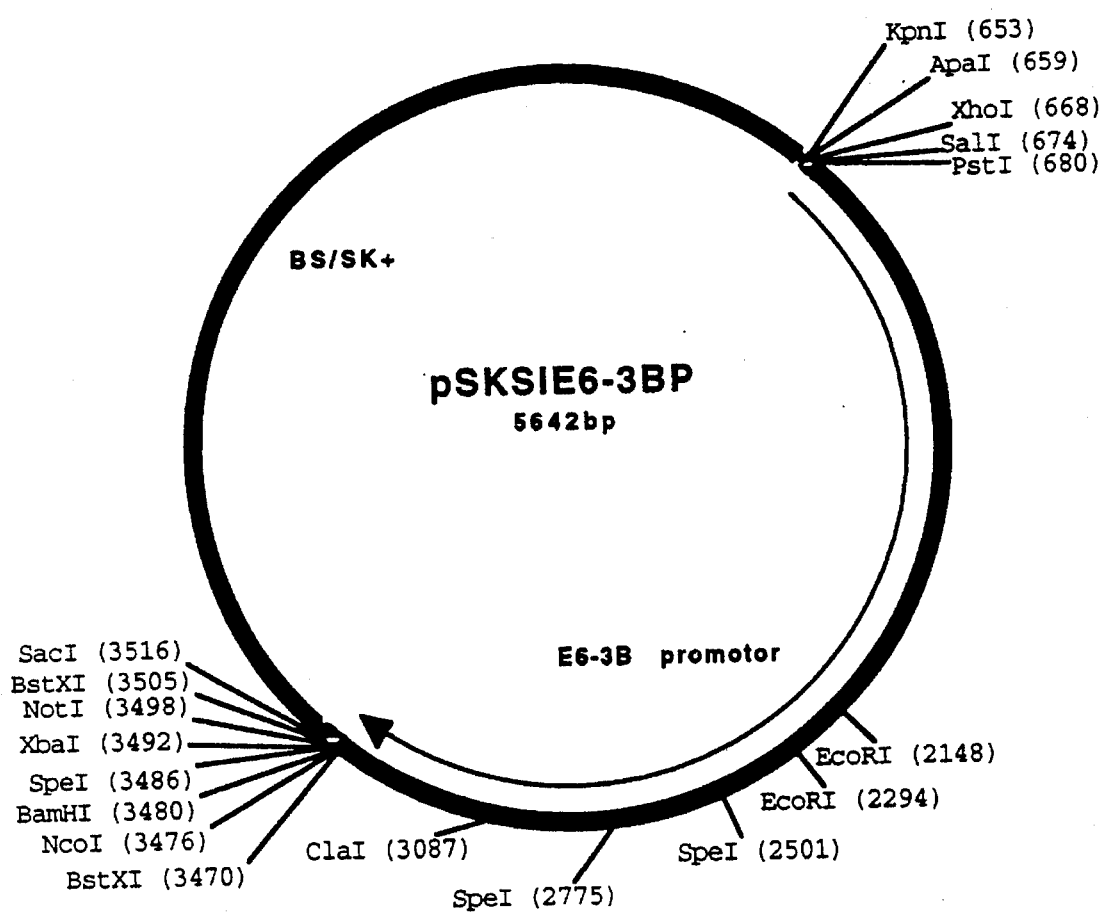
FIG. 1 is a diagram of pSKSIE6-3B promoter plasmid.

The present invention is directed toward the creation of transgenic fiber-producing plants with altered fiber characteristics, preferably stronger fiber. The altered fiber characteristics are caused by the transformation of plants with genes necessary to express a heterologous peroxidase. By "heterologous," we mean a peroxidase gene that has been inserted into a plant through recombinant molecular biological techniques. This peroxidase gene can be homologous or nonhomologous to a peroxidase gene natively present in the fiber-producing plant. The Examples below show altered fiber properties due to the integration of a cotton cationic peroxidase gene in DP-50 cotton. Other peroxidase genes are suitable for the present invention.

To produce transgenic plants as described herein, three components are needed. The first component is a protein coding sequence or sequences which are sufficient to allow the production of peroxidase in fiber-producing plant cells. The second element is a promoter capable of causing expression of the transgenes in the fiber cells of the plant. In order that the transgenes responsible for peroxidase production do not disrupt the morphological characteristics of the fiber-producing plant, the protein coding sequence for the gene is preferably placed downstream from a tissue-specific promoter which promotes preferential expression of the gene in fiber cells. The third element is a transformation process by which a gene construct can be transferred into the germ-line of a fiber-producing plant. All three of these elements will be discussed below.

Previous research with transgenic plants has demonstrated that transgenic plants are capable of passing on the inserted genes to their progeny by normal Mendelian inheritance (Christou, et al., *Trends in Biotechnol.*, 8:145–151, 1990). All such progeny plants which inherit the inserted genetic construct are also transgenic plants as the term is used here.

Increasing the strength of cotton fiber is one goal of the present invention. Increased fiber strength is one of the most important properties desired by the textile manufacturers. Table 1, below, shows the strength profile of a number of cotton cultivars presently cultivated in this country. As seen from Table 1, the "upland" varieties of cotton have generally low strength in comparison to the "barbadense" type of cottons. Conferring greater strength to upland variety fiber may allow the processing of cotton fibers, such as spinning and weaving and other fabric-making processes, to be conducted at higher machine speeds. This in turn results in lower manufacturing cost. Additionally a stronger fiber also result in a stronger fabric and may show less wear and tear and last longer.

In addition to the increased fiber strength already demonstrated in the Examples below, it is envisioned that additional qualities of fiber are altered. Such possibilities include altered water absorption. The water absorption profile of the transgenic fiber may be different than normal fibers due to the rigid primary wall resulting from increased cross-linkages. Similarly, transgenic fibers may have less crimp. This in turn may result in less shrinkage of the fiber or the fabric.

A. Fiber Specific Promoters.

1. In General

Promoters are DNA elements that initiate the transcription of a downstream protein coding sequence, a first step in the expression of genes. Promoters suitable for use in the present invention are capable of directing peroxidase expression in transgenic fiber-producing plants, preferably in a fiber-specific manner. Fiber-specific promoters will ensure that the peroxidase is preferentially synthesized in fiber cells and, therefore, does not cause abnormal physiology in other tissues. Such abnormalities are known to occur in plants when peroxidase is over-expressed by a constitutive type promoter (Lagrimini, et al., *Plant Cell.,* 2:7–18, 1990). Also, it is helpful that the promoters that direct the synthesis of peroxidase be developmentally regulated. It is helpful to have a battery of fiber-specific promoters of varying strengths in order to manipulate the concentrations of various peroxidases.

We have isolated promoters from cotton that meet these criteria using the methods detailed below. Other suitable fiber-specific promoters may be isolated by this method or by using known cotton promoter sequences, such as SEQ ID NOs: 4 or 5, to probe a genomic library obtained from a fiber-producing plant for homologous sequences.

In brief, fiber-specific cDNA clones are isolated from a fiber cDNA library through differential screening. Genomic clones are isolated by using the fiber-specific cDNA clones as probes to screen a cotton genomic library. Because it is known that promoter activity is found on the genomic DNA within the nucleotide sequence upstream from the start of RNA transcription, the cDNA and genomic clones are structurally characterized to enable us to isolate and identify these upstream genomic nucleotide sequences with potential promoter activity.

To determine whether the isolated sequence contains promoter activity, a chimeric gene construct containing the marker gene *E. coli* beta-glucuronidase (GUS) and a putative fiber promoter is introduced into cotton hypocotyl tissue. Detection of GUS activity by histochemical staining demonstrates that the promoter is active. The sequence of two exemplary fiber-specific promoters, E6-3B and B8, are presented below at SEQ ID NOs: 4 and 5 to make such a promoter generally available.

2. RNA Isolation From Fiber

The first step in the isolation of fiber-specific promoters is to isolate RNA from cotton fiber cells (See, for example, John, *Nucl. Acid. Res.,* 20:2381, 1992). We chose to isolate RNA from specific developmental stages of cotton fiber because we wanted a selection of fiber-specific promoters capable of regulation at different developmental stages. Nevertheless, if one wishes to obtain fiber-specific RNAs, RNA may be isolated from fiber cells at any stage of fiber development.

Ten-, fifteen- and twenty-three-day-old fiber cells from Coker 312 plants are collected and quick-frozen in liquid nitrogen. The 10-day fiber cells were selected to contain genes active during the primary cell-wall stage of cell development. In the 15-day cells, both primary cell-wall and secondary cell-wall synthesis systems are active. The 23-day-old fiber cells were selected to contain genes principally active during secondary wall synthesis.

The frozen fiber cells are powdered in a mortar in liquid nitrogen and homogenized for 1.5 minutes using a polytron in a homogenization buffer at full speed. The homogenization buffer is added at a ratio of 1:2 of tissue (weight) to buffer (volume). Homogenization buffer is: 5M guanidine isothiocyanate, 0.2M Tris-acetate (pH 8.5), 0.7% Beta-mercaptoethanol, 1% polyvinyl pyrrolidone (PVP, MW 40 Kd), and 0.62% sodium lauryl sarcosine. Beta-mercaptoethanol and PVP are added just before use.

The homogenate is filtered through Mira cloth and layered over a 1.5 ml pad of 5.7M cesium chloride as described by Chirgwin, J. M., et al. *Biochemistry.,* 18:5294–5299 (1979). The homogenate is then centrifuged for 18 hours at 36,000 rpm in a SW 50.1 rotor at 20° C. After centrifugation, the RNA is collected as described by Chirgwin, et. al., (supra). The RNA is then further purified by phenol:chloroform extractions and precipitations in the presence of ammonium acetate, as described for DNA by Crouse, J. and Amorese D., *Focus,* 9[2]:3–5 (1987).

Poly $(A)^+$RNA is obtained by oligo-(dT) chromatography as described by Maniatis, et al., in *Molecular Cloning: A Laboratory Manual.,* Cold Spring Harbor Laboratory, Cold Spring Harbor, N.Y., (1982).

3. Library Construction and cDNA Clone Identification

It is necessary to screen the isolated fiber RNA to determine which RNA sequences are fiber-specific. (By the term "fiber-specific" we mean a sequence that is present either only in fiber cells or in a much higher abundance in fiber cells than in other plant cells.) A standard technique used to identify tissue-specific sequences is to create cDNA clones from the RNA molecules isolated from a particular tissue and then to challenge the individual cDNA clones with radioactive cDNA created from RNA isolated from other tissues. cDNA clones that hybridize to fiber cDNA, but not cDNA derived from RNA from other plant tissues, contain a cDNA made from an mRNA that is fiber-specific. These mRNAs will likely be under the control of a fiber-specific promoter.

Complementary DNA libraries may be prepared by any standard technique. We chose to prepare separate cDNA libraries from the mRNAs from 10-day, 15-day and 23-day-old fiber cells according to the protocol developed by D'Alessio, et al., *Focus,* 9[1]:1–4 (1987) with the following exceptions: The first strand of cDNA is synthesized with a primer of the sequence set forth in SEQ ID NO: 1 below. For the 10-day-old fiber cell mRNAs, an oligo-(dT) primer is used instead. The second strand synthesis is carried out as described by D'Alessio, et al., supra, for homopolymer tailing. Poly-(dC) tails are added to the double-stranded cDNA, which is annealed to poly-(dG)-tailed pBR322 plasmid vector (Bethesda Research Laboratories). *E. coli* RRl strain is transformed with the recombinant plasmids as described by Hanahan in *DNA Cloning-A Practical*

*Approach*, Vol. 1 (1985) p. 109–135. The transformed cells were selected on antibiotic tetracycline (12 mg/liter) containing agar plates.

The specific bacteria that harbored plasmids containing fiber-specific cDNAs are identified by differential screening. The clones in the library are transferred to nitrocellulose filters and duplicate filters were made according to Hanahan and Meselson, *Gene*, 10:63–67 (1980). We screened about 25,000 clones from the 15-day and 23-day libraries using the following procedure: Radioactive probes are prepared from poly(A)$^+$ RNA of 15-day-old and 23-day-old fiber producing cells and from poly(A)$^+$ RNA of 0-day ovule, leaf, root and flower cells. The radioactive probes are prepared as described in Maniatis (supra) from $^{32}$P-dCTP and reverse transcriptase. The radioactive probes are exposed to the filters containing the clones. Prewashing, prehybridizations, hybridizations and washings of the filters are performed as described in detail in John, et al., *Proc. Natl. Acad. Sci. USA*, 81:5628–5632 (1984).

The autographic signals from duplicate filters hybridized with $^{32}$P-labelled cDNAs from the different tissues are compared and the clones which hybridized to cDNAs from fiber-producing cells, but not to cDNAs from other tissues, are identified and isolated. The identified clones are then subjected to three more cycles of differential screening as described above. This repetitive screening eliminated clones which hybridized to cDNAs from non-fiber-producing cells.

Alternatively, another method of screening a cDNA library for fiber-specific cDNA clones is by subtractive hybridization. In general, fiber cDNA is challenged with excess RNA from different tissues. Fiber cDNA that does not hybridize to the RNA preparations remains single-stranded. These non-hybridizing cDNA sequences are more likely to be fiber-specific. This procedure has been described by Duguid, et al., *Proc. Natl. Acad. Sci. USA*, 85 pp. 5738–5742 (1988).

We screened the cDNA library from the 10-day old cells using a subtractive hybridization procedure. In our procedure we first hybridize the $^{32}$P-labelled cDNA from fiber to excess biotinylated mRNA isolated from leaf tissue. The hybridized cDNA-biotinylated mRNA hybrids are reacted with streptavidin, which is a protein with a high affinity for biotin, and the biotinylated mRNAs are separated from unhybridized cDNA by extraction with avidin in phenol:chloroform. The streptavidin and biotinylated mRNA were partitioned into the organic phase while the single-stranded cDNA remained in the aqueous phase.

Subtractive hybridization screening of 4788 clones of the 10 day fiber cell cDNA library with leaf cell cDNAs resulted in the identification of 800 putative clones not present in the leaf cells. These clones were then screened with cDNAs generated from ovule, flower and root mRNAs. 79 putatively fiber-specific clones were obtained from this screening.

After obtaining fiber-specific clones, it is useful to examine RNA populations of the different tissues to determine whether the RNA encoded by the selected cDNA clone is within the population. This procedure is a double-check that the RNA is fiber-specific. The standard molecular biological method for examining a population of RNA for the presence of a particular sequence is a northern blot. For this analysis, poly(A)$^+$ RNA from different tissues is denatured in the presence of formaldehyde and size-fractionated by electrophoresis on 1.5% agar/formaldehyde gels. (John, et al., supra). The RNAs are blotted onto nitrocellulose and probed with $^{32}$P-labelled inserts of each individual clone. The clones that hybridized to only RNAs from fiber-producing cells are selected. All manipulations on plasmid DNAs such as isolation, purification on cesium chloride gradients, restriction digestion, insert purifications by gel electrophoresis and electroelutions, and $^{32}$P-labelling by nick translations are standard techniques (e.g., see Maniatis, et al., supra and John, et al., supra).

Several cDNA clones may correspond to the same RNA sequence. The number of unique RNAs represented among the selected cDNA clones may be determined by cross-hybridizing the cDNA clones. Clones that hybridize to each other are generated either from the same RNA sequence or from a related RNA sequence. We detected cross-hybridizing clones by a polymerase chain reaction (PCR) procedure (Saiki, et al., *Science.*, 239 pp. 487–491 (1988)), Southern blotting and hybridization. The PCR reaction is carried out by first mixing 10 µl of bacterial culture of the cDNA clone with 90 µl of distilled water. Twenty µl of that mixture is added to a PCR reaction buffer of 50 mM KCl, 10 mM Tris-HCl pH 8.0, 2.5 mM MgCl$_2$, 0.01% gelatin, 200 µM each of dATP, dCTP, dTTP and dGTP, 12.5 picomolar each of sense and antisense primers for pBR322, and 0.5 units of Taq polymerase. The final reaction volume is 52 µl. The PCR reactions are carried out under standard conditions in a Perkin-Elmer-Cetus thermocycler.

The amplified DNA from the PCR reactions is separated by agarose gel electrophoresis and blotted onto nitrocellulose as in Southern, *J. Mol. Biol.* 98:503–517 (1975). One or more DNA inserts of the bacterial clones from the same group are amplified by the same procedure and the products also separated on agarose gel. The amplified insert DNAs are then excised from the gel and purified by electroelution. The purified DNAs, labelled with $^{32}$P by nick translation, are hybridized with the Southern blot and the cross-hybridizing clones identified.

After northern hybridization and tests for cross-reactivity, we had approximately 20 putative fiber-specific clones. This number represents cDNAs from all three fiber cDNA libraries.

Although we characterized all the fiber-specific cDNAs and obtained genomic clones corresponding to many of these cDNAs, only two cDNA clones will be discussed further. These clones are E6 and B8. These cDNA clones and their corresponding genomic clones will serve as examples of the isolation and use of fiber-specific promoters.

a. CKFB15A1-E6 cDNA clone (E6 cDNA)

This cDNA clone for a fiber gene has an insert of 983 base pairs which hybridizes to 1.0 and 1.1 kb RNAs. The RNA is expressed in fiber and not in root. Flower, leaf and ovule RNAs show weak hybridization.

The E6 RNA was found to be developmentally regulated. Its steady-state concentration increases immediately after anthesis. Our quantification of E6 transcript in fiber using in vitro synthesized E6 RNA as a control shows that 20 ug of RNA from 20-day-old fiber contains about 3.5 ng of E6 RNA. Thus, E6 RNA is an abundant fiber RNA.

Hybrid selection translation experiments showed that E6 codes for two polypeptides of 26 and 30 kDa. The E6 cDNA clone cross-hybridizes with Pima and Naked seed cotton fiber cell RNAs. The clone also cross-hybridizes with a number of plants belonging to *Gossypium* species. Thus, DNAs from Pima and Sea Island (*G. barbadense*) PD3 and DP50 (*G. hirsutum*) and plants belonging to *G. longicalyx* and *G. somalense* all showed hybridization. In addition, plants belonging to another species of family *Malvaceae*, the *Hibiscus*, are also found to have conserved the E6 gene.

DNAs of *H. sabdariffa* L. cv., Rosselle, Kapok (*Ceiba pentandra*) belonging to family *Bombacaceae*, and Hemp (*Cannabis sativa*) belonging to family *Moraceae* also showed hybridization to E6 gene. We confirmed that E6 or a homologous gene is present in *Gossypium darwinii*, *Gossypium herbaceum* L. cv. *Jayadhar* and *Tzuyung*, *Gossypium anomalum*, *G. australe*, *G. nelsonii*, *G. arboreim* L., cv., *Nanking* and *Liaochung*, *G. thurberi*, *G. davidsonii*, *G. raimondii*, *G. stocksii*, *G. somalense*, *G. longicalyx*, and *F. bickii*. Thus, the E6 sequence is conserved in most of the plants belonging to family *Malvaceae* and also found in two other families *Bombacaceae* and *Moraceae*. Many of these plants produce seed hair or bast fiber. Interestingly, we did not detect E6 hybridization in the DNAs of soybean, corn, tobacco or the cellulose-producing bacterium Acetobacter (*A. xylinum*). These studies imply that E6 gene may have functions in the formation of seed hair or bast fiber cells (John and Crow, supra).

The complete nucleotide sequence of E6 insert is presented as SEQ ID NO: 2. This sequence contains a long open reading frame extending from position 1 to position 748. On this same open reading frame, start codons appear at positions 34, 61 and 94. If the first codon is the initiation site for the protein, the 714 nucleotide reading frame would yield a 238 amino acid protein. E6 cDNA clone was deposited with ATCC at Accession Number 67809.

SEQ ID NO: 2 also contains an additional 84 residues and a stretch of poly(A) that originate from clone PCKFB15-B3. This clone is identical to pCKFB15A1-E6 except for the presence of additional residues at the 3'-end.

b. CKFB15A1-B8 cDNA clone (B8 cDNA)

B8 RNA is 1100 bases long and is developmentally regulated. It is not expressed in leaf, root, ovule or flower. B8 cross-hybridizes to Pima, PD3 and Sea Island genomic DNAs and is encoded by one or two genes. The B8 cDNA clone has an insert of 690 bp, the sequence of which is presented at SEQ ID NO: 3 below. It has been deposited with ATCC at Accession Number 67807.

4. Preparation of Genomic DNA and Creation of Genomic Clones.

To isolate a promoter sequence, one must isolate the DNA sequence upstream from the site of RNA transcript initiation. We accomplished this by probing a library of cotton genomic clones with the fiber-specific cDNA clones. The description below describes a genomic library created from Sea Island cotton, but other cotton varieties would be suitable. We have also probed Coker 312 (another cotton variety) and Kapok (a related fiber-producing plant) libraries with our clones. We believe that fiber-specific promoters isolated from different cotton varieties are effective in other cotton varieties.

Genomic DNA from Sea Island cotton is prepared according to the methods of E. Richards described in *Current Protocols in Molecular Biology*, (Eds. Ausbel, F. M., et al.) Wiley, (1987) pp. 2.3.1–2.3.3, with the following modification: the frozen plant material was homogenized in extraction buffer containing 1% polyvinyl pyrrolidone. The purified genomic DNA is digested with restriction endonucleases and transferred to nitrocellulose filters by the Southern blotting technique. Southern, E. M., *J. Mol. Biol.*, 98:503–517 (1975).

The filters are then probed with nick-translated inserts of the fiber-specific cDNA clones. The hybridization and blot washing conditions are described in John, et al. (supra).

Upon such a hybridization, we found that our fiber-specific cDNAs were represented in the cotton genome.

Sea Island cotton genomic libraries are prepared by ligation of the digested cotton DNA into a vector. We chose to have our cotton genomic library constructed by Clonetec, Inc., of California, in EMBL-3 vectors. When the fragments were initially cloned, a Sal I site was added to the fragment by the cloning vector. The designation "Sal I (Mbo I)" indicates that a naturally occurring Mbo I site exists adjacent to the artificial Sal I site. (The genomic fragments were originally created by a partial Mbo I digest.) Genomic inserts of about 10–15 kb were present in the EMBL3 phage library. The phage libraries are plated on *E. coli*. We chose to plate our phage library on *E. coli* NM 538 as described in *Current Protocols in Molecular Biology*, (supra, p.6.0.1–6.8.5).

The phage library was screened with radioactive fiber-specific cDNA inserts. A number of phage that hybridized to B8 and E6 cDNA clones were identified. Genomic clones that we chose to examine further are described below. The nomenclature for the genomic clones is as follows: EMBL= Lambda vector; SI=Sea Island; E6=cDNA insert that hybridizes to genomic clone; the last number corresponds to different genomic clones from a given library. We obtained many different genomic clones corresponding to our fiber-specific cDNA clones. From these genomic clones, we isolated regions with promoter activity. SEQ ID NOs: 4 and 5 give sequence information for the E6-3B and B8 fiber-specific promoters.

For some of these clones, we have identified cross-hybridizing genomic clones from other cotton species. For example, we have two different genomic clones from the Sea Island cotton library that hybridize to E6 cDNA, as well as two genomic clones from the Coker 312 cotton library and one genomic clone from a Kapok library.

As an example of the isolation of fiber-specific promoters, below we give more detail concerning the isolation of two fiber-specific promoters—the B8 and E6 gene promoters. One wishing to practice the present invention could isolate fiber-specific cotton promoters from a cotton genomic library by either going through a differential screening and obtaining a fiber-specific cDNA to use as a probe, as we have described, or using sequences corresponding to those described here as probes to isolate corresponding promoters from the cotton genome.

5. Characterization of Fiber-Specific Promoters.

(a) In General

Once a genomic clone has been isolated, one must identify the DNA fragments that contain promoter activity within the large genomic insert. Comparison of the genomic clone with the corresponding cDNA clone will demonstrate which part of the genomic insert contains the upstream sequence. This comparison may be done through restriction mapping of both clones or hybridization of the cDNA clone to different restriction fragments of the genomic insert. Once a fragment with promoter activity has been identified, this fragment may be subcloned into a more convenient vector system.

(b) E6 Gene Promoters

We have identified two independent genomic clones from a Sea Island cotton genomic library, pEMBLSIE6-2 and pEMBLSIE6-3, that hybridize to E6 cDNA. Both phages contain 15 kb inserts. In this discussion, we will focus on pEMBLSIE6-3.

One of the E6 genes, pEMBLSIE6-3, was subcloned into Bluescript Sk$^+$ vector as follows: A 5.0 kb Sal I fragment that hybridized to E6 cDNA was ligated into the Sal I site of Bluescript resulting in pSKSIE6-3B. An Nco I/Sal I fragment (2.7 kb) contains the promoter of E6-3B gene. FIG. 1 is a diagram of this construction. SEQ ID NO: 4 is the sequence of the 5'-end of E6-3B gene. Comparison of the nucleotide sequences of E6-2 and E6-3B promoter regions (about 600 bp) shows no differences. However, it is clear that there are restriction polymorphisms between these genes further upstream. Furthermore, we have also identified sequence differences in the 3'-ends of these genes. E6-2 and E6-3B promoters also show differences in their ability to express GUS gene in transient assays. E6-3B promoter is 3-fold stronger than E6-2 promoter.

(c) B8 Gene Promoter

Figure 2:
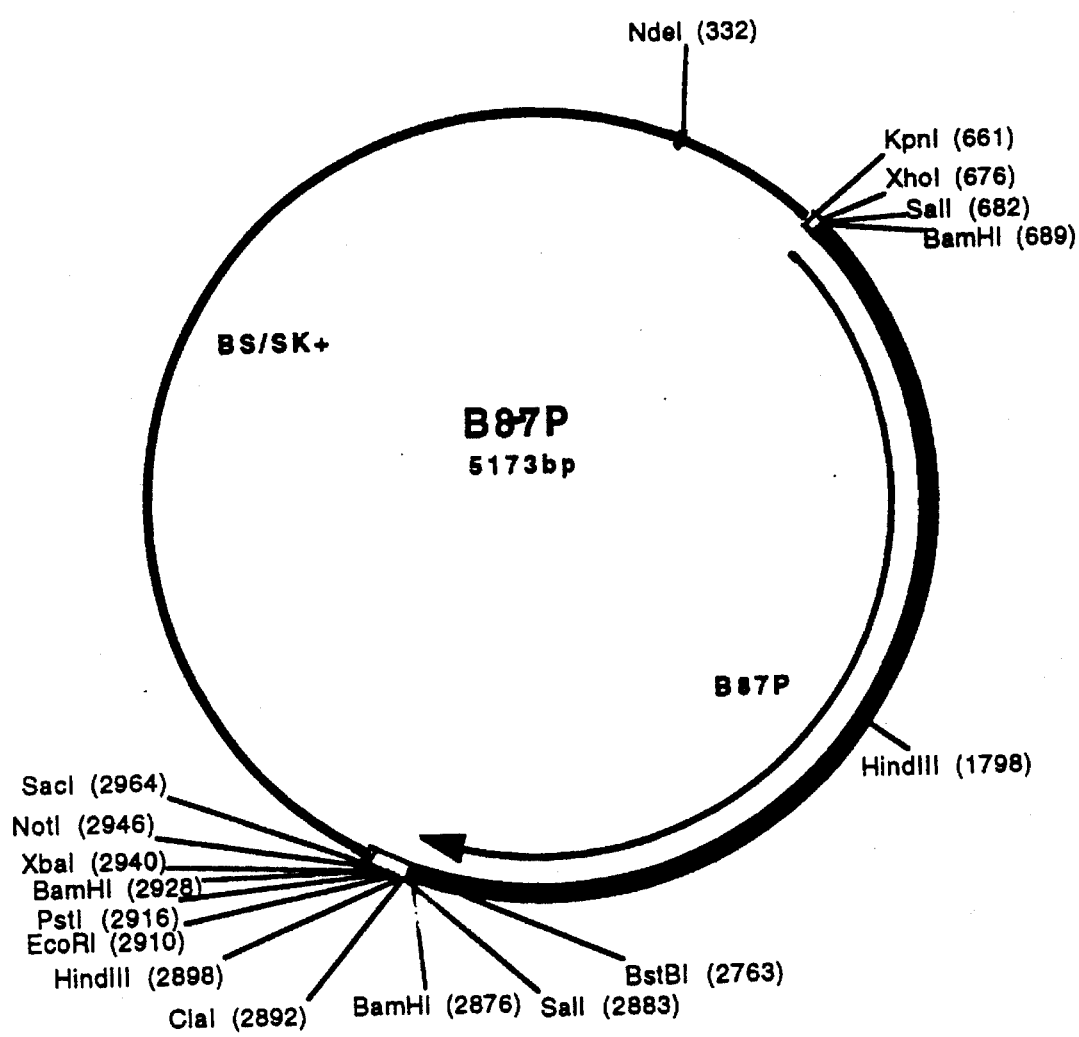
FIG. 2 is a diagram of pSKSIB8-7 promoter plasmid.

EMBLSI-B8 was isolated from Sea Island genomic library as hybridizing to the B8 cDNA clone. A 9.5 kb Sal I/Bam HI fragment from the genomic clone was inserted into the SK vector to form pSKSIB8-HI. A 2.2 kb Bam HI/Bst BI fragment from the clone was assayed for promoter activity (FIG. 2). SEQ ID NO: 5 is the partial sequence of this promoter fragment.

(d) Determination of E6 and B8 Promoter Activities

Once one has obtained a fragment of DNA with putative promoter function, it is necessary to determine whether the sequence is capable of controlling transcription. This may be accomplished by ligating the putative promoter into a plasmid containing a marker gene, but no promoter, and assaying for the expression of the marker gene. We constructed such a system, along with the appropriate controls, to assay the function of our fiber-specific promoters.

Figure 3:
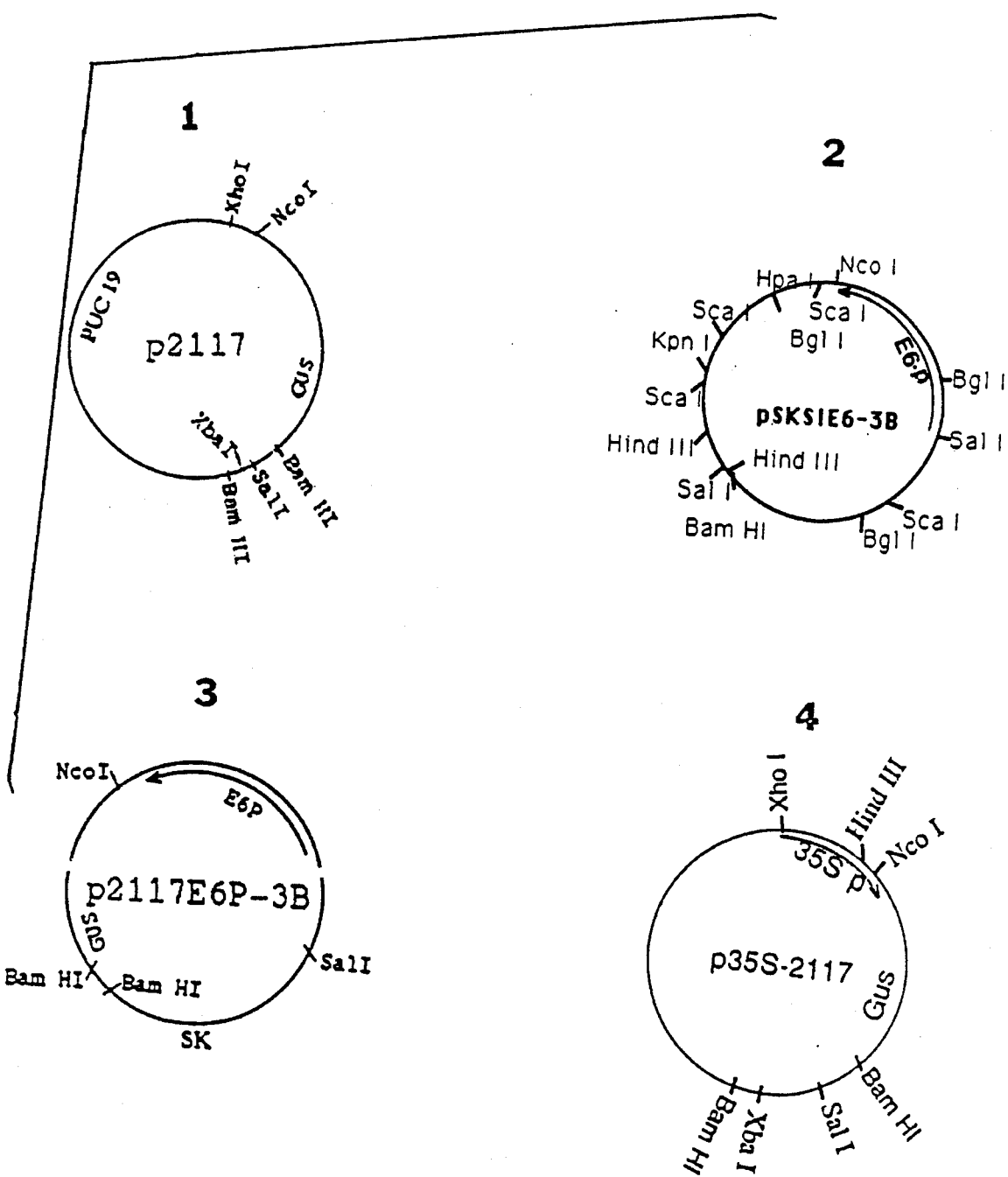
FIG. 3 is a diagram of plasmids useful in an assay for promoter activity.

FIG. 3 describes the plasmids used in that system. Basically, the system uses four plasmids. The first plasmid, p2117, contains a marker gene without a promoter. The second plasmid contains the putative promoter. The third plasmid contains the putative promoter and a marker gene. The fourth plasmid, p35S-2117, contains a proven viral promoter and a marker gene. After bombardment of the test tissue with the different plasmids, expression by the third and fourth plasmids and not by the first and second indicates that the tested fragment has promoter ability. The Nco/Sal fragment (2.7 kb) of the E6 promoter and Bam HI/Bst BI fragment (2.2 kb) of the B8 promoter were subjected to this assay and found to have promoter ability. Cotton hypocotyl tissue was bombarded with the plasmids via particle-mediated methods, discussed below. Obviously, this system is not suitable for assaying whether or not the promoter is tissue-specific. In vivo plant experiments, in which the presence of the gene product in different tissues is examined, will determine whether the promoter is fiber-specific.

We investigated whether E6-3B promoter can be used to express a foreign gene in cotton fiber as follows: the E6-3B promoter was fused with the coding region of a carrot cell-wall protein gene, extensin, and introduced into cotton. Various tissues of plants regenerated were examined by northern blots experiments to detect extensin RNA. We found that only fiber cells contain extensin RNA. John and Crow, *Proc. Natl. Acad. Sci. USA,* 89:5769–5773, 1992. These results support the claim that E6-3B promoter can direct expression of foreign genes in a tissue specific manner in transgenic cotton.

B. Peroxidase Genes

Peroxidase genes from a wide variety of sources are suitable for the present invention.

Peroxidase genes have now been cloned and sequenced from cucumber (*Cucumis sativus,* Morgens, et al., *Plant Mol. Biol.,* 14:715–726, 1990), peanut (Buffard, et. al., *Proc. Natl. Acad. Sci. USA,* 87:8874–8878, 1990), horseradish (*Amoracia rusticana,* Fujiyama, et. al. *Eur. J. Biochem.,* 173:681–687, 1988), potato (anionic peroxidase) (*Solanum tuberosum* Roberts, et al., *Plant Mol. Biol.,* 11, 15–26, 1988), hybrid poplar (anionic peroxidase) (Kawai, et al., *Biosci. Biotech. Biochem.,* 57:131–133, 1993), *Arabidopsis thaliana* (neutral peroxidase), (Intapruk, et al., *Gene,* 98:237–242, 1991); tobacco (cationic peroxidase), (*Nicotiana tabacum,* Lagrimini, et al., *Proc. Natl. Acad. Sci. USA,* 84:7542–7546, 1987), tomato (*Lycopersicon esculentum,* Roberts and Kolattukudy, *Mol. and Gen. Genet.,* 217:223–232, 1989), wheat (*Triticum aestivum,* Hertig, et al., *Plant. Mol. Biol.,* 16:171–174, 1991), barley (*Hordeum sativum,* Rasmussen, et al., *Plant. Mol. Biol.,* 16:320–327, 1991), white rot basidiomycetes *Phanerochaete chrysosporium,* (Ritch and Gold, *Gene,* 118, 73–80, 1992), and *Trametes versicolor* (Black and Reddy, *Biochem. Biophys. Research Comm.,* 179:428–435, 1991). Peroxidases from the organisms described above (or analogous organisms) can be obtained by using the published sequence to create nucleic acid probes that are capable of identifying a peroxidase gene or cDNA sequence in an appropriate library. Well-known methods of molecular biology may be used to attach this peroxidase sequence to fiber-specific promoters (such as those described above) and obtain expression of the peroxidase gene.

Most of the plant peroxidase show considerable nucleotide and amino acid sequence homology. Residues near the distal and proximal heme ligand are conserved. Tyson found that 123 amino acids representing 41% of the average 300 amino acids in 13 plant peroxidase are conserved. (*Can J. Bot.,* 70:543–556, 1992). Thus, peroxidase cDNA clones or genes show cross-reactions and can be used to isolate other peroxidase cDNAs.

In the Example below, we have obtained a cationic cotton peroxidase gene. In addition we have isolated six peroxidase cDNA clones from a tobacco cDNA library, as well as two peroxidases from *Arabidopsis.* We have DNA sequences from the two tobacco peroxidases.

C. Construct Formation

Once the desired gene and fiber-specific promoter are identified, it is necessary to combine these elements into a construct so that the fiber-specific promoter can control the transcription of the gene. This is typically done by standard molecular biological techniques. Preferably, the peroxidase gene is ligated downstream from the fiber-specific promoter in a plasmid or viral vector. We envision that an altered cotton fiber might require more than a single heterologous gene. Therefore, the cotton plant might advantageously be transformed with constructs containing more than one peroxidase gene or more than one construct.

Preferably, the coding regions of peroxidase genes will be fused with fiber-specific promoters in such a manner that transcription will occur from an untranslated leader sequence contained in the 3'-end of the promoter. This untranslated region also was identified from fiber genes. At the 3'-end of the coding region of the peroxidase gene, if necessary a 3' untranslated region of a fiber gene can be preferably fused. This region contains a poly-(A) additional signal that enables transcription to stop. Sequence of the 3' untranslated region that we used in our peroxidase gene expression vector is shown in SEQ ID NO: 6 and was identified from the fiber-specific genomic clone pSKSIE6-3B. The 3' untranslated regions of other plant genes would also be suitable.

Figure 4:
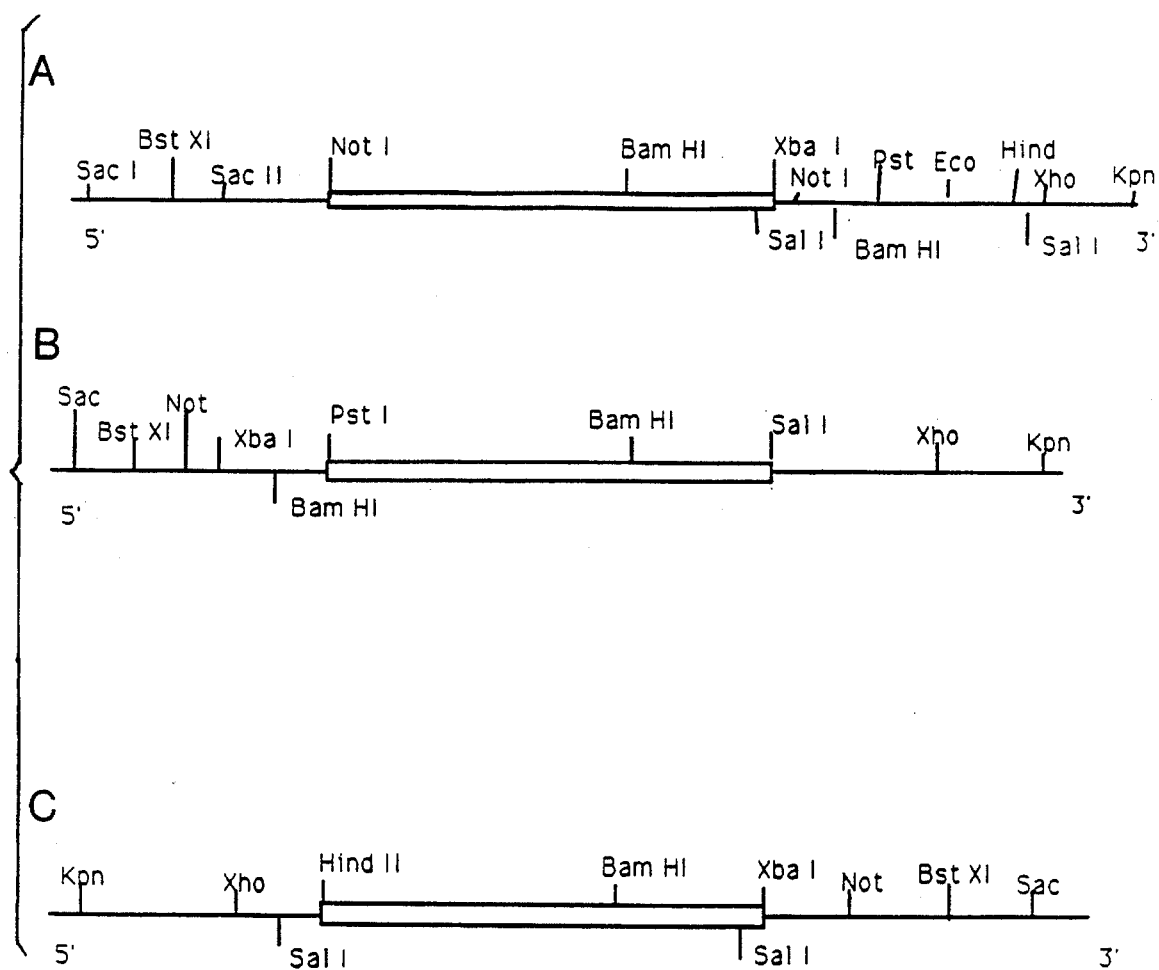
FIG. 4 is a diagram of three constructs with the E6-EB 3'-end along with NOS (A) fragments.

As an added precaution that correct transcription stop will occur, we added a nopaline synthase (NOS) poly-(A) addition signal (Depicker, et al., *J. Mol. Appl. Genet.,* 1:561–573, 1982). Preferably, a sequence such as this should be used to correctly process the 3'-end of the message. The NOS poly-(A) sequence has been proven to function as an authentic plant transcription stop signal (McCabe, et al. *Biotechnology*, 6:923–926, 1988). Fragments containing the 3'-end of E6 gene and the NOS poly-(A) fragment were cloned into a number of restriction sites in the SK vector and are shown in FIG. 4.

Most transformation methods work on a statistical basis. A certain low percentage of the target cells will become transformed. To identify these transformed cells, it is useful to insert a marker or selection gene in the construct. A marker gene which has been found useful in such plant transformation is the GUS gene as described by Jefferson, et al., *EMBO J.*, 6:3901–3907 (1987). The GUS gene encodes the enzyme beta-glucuronidase, which can be expressed in plant cells. The expression of the GUS gene can be determined in a tissue destructive but convenient histochemical assay of plant tissues. The product of the GUS gene will change the color of a substrate, 5-bromo-4-chloro-3-indolyl glucuronide, to blue in an in situ assay in plant tissues. Thus, the use of a GUS gene provides a convenient colorimetric assay for the expression of introduced DNA in plant tissues by histochemical analysis of the plant tissues.

In a typical transformation process, the desired gene of interest sought to be expressed in the plant could be coupled in tandem in a single genetic construct with the GUS gene. The coupled tandem genetic construct could then be transformed into plant tissues and the resultant plant tissues would be analyzed for expression of the GUS enzyme in the target plant tissues to identify transgenic tissues.

Another way to identify the presence of the construct in a plant cell is to use a selectable marker gene. A selectable marker is one that conditions for a trait in the transformed plant cells which can be selected by the exposure of the plant tissues to a selection agent. Suitable selectable markers would be antibiotic resistance genes or herbicide resistance genes which, when inserted in some cells of a plant in culture, would imbue those particular cells with the ability to withstand exposure to the antibiotic or the herbicide which would kill all the nontransformant cells in the culture. Selectable markers are generally preferred for plant transformation events, but are not available for all plant species.

D. Transformation (1) In General

We chose to use accelerated particles to transform cotton with the DNA constructs. McCabe and Martinell, *Bio/Technology*, 11:596–598, 1993. A style of apparatus for accelerating such particles has been described in detail in U.S. Pat. No. 5,015,580 (hereby incorporated by reference). In brief, small metal particles are coated with nucleic acid material and accelerated into target cells. By an unknown mechanism, a certain percentage of the target cells will incorporate the nucleic acid.

Other particle acceleration apparatus, such as the commercially available BioRad (Biolistics) PDS-2000 particle acceleration instrument, will be suitable for the present invention. Other non-accelerated particle methods are also suitable. Such methods include electroporation, viral vectors, and *Agrobacterium*-mediated transformation.

Stable integration and expression of foreign genes in cotton plants has been demonstrated and repeated. Umbeck, et al., *Bio/Technology*, 5[3]:263–266 (1987); Firoozabady, et al., *Plant Mol. Biol.*, 10:105–116 (1987). In each of these references, the transformation of cotton tissues is accomplished by *Agrobacterium* infection and regeneration. Although a lengthy process, the *Agrobacterium*-mediated transformation of cotton has also been practiced by other laboratories and can now readily be replicated by those of ordinary skill in plant genetic engineering.

It is to be understood, however, that new methods for the transformation of cotton plants and lines are being studied, and that the transgenic cotton plants and lines with introduced peroxidase genes will prove advantageous and useful regardless of the method of transformation of the original tissues. The description below suggests a preferable method of transformation.

(2) Surface Sterilization

We have developed a cotton transformation system that is particularly advantageous for the practice of the present invention. The process begins with commercial cotton seed, which must be sterilized. In our example, we used DP-50 cotton seeds, although other varieties would be equally suitable. We chose DP-50 because it is a cotton variety with good growing characteristics but a coarse fiber.

A sieve beaker system is autoclaved. A sieve beaker system is a beaker with dozens of holes drilled in its bottom that can be nested inside a non-drilled glass beaker. It is also useful to utilize a third sterile beaker for rinsing the seeds so that the sieve beaker can be rested in the sterile beaker while discarding wash water.

The sieve beaker is filled with cotton seeds. The beaker into which the sieve beaker is nested is then filled with a mixture of 50% Chlorox bleach so as to cover the seeds. The seeds are allowed to rest within the bleach solution for three minutes. The bleach is drained and the seeds are then rinsed five times with distilled water.

The surface sterilized cotton seeds are then placed in a sterile glass beaker. A cotton antibiotic sterilization medium is added to the beaker at twice as much volume as there are seeds. This medium consists of sterile distilled water to which has been added carbenicillin at 200 mg per liter, cefotaxime at 125 mg per liter, and 30 mg each of BRAVA WP fungicide, BENLATE 50 DF fungicide, and CAPTAN 50 WP fungicide per liter. The seeds are incubated in the sterilization medium for three to four hours in the dark at room temperature.

Then the seeds are drained by pipette. The beaker is refilled with fresh cotton antibiotic sterilization medium and the seeds are incubated for an additional three hours.

The seeds were then drained and incubated overnight at 15° C. in the dark to germinate. If germination proceeds appropriately, the seed germination could be stopped by refrigeration at 4° C., for up to three days following the germination process.

(3) Seed Dissection

After the germination of the seeds, or the removal of the germinated seeds from storage, seeds are selected that are just beginning to germinate. Overly germinated or ungerminated seeds are discarded. The proper stage of germination is defined as fully imbibed seeds with one to four millimeters of the radicle exposed. Under sterile conditions, the seed axis is removed out of the seed. This is done by manual manipulation with gloved hands to remove the seed axis from both of its cotyledons and its seed coat. The process is relatively easy to perform with practice. It is possible to readily develop the ability to pop the seed coat axis apart from the seed, without damaging the seed axis, or leaving any of the cotyledon on the seed axis.

The excised seed axis is then washed in three to four rinses of sterile distilled water. The washed but undissected explants are either dissected immediately or stored by plating on standard OR ccb medium made with fresh benzylaminopurine or BAP, but no NAA. This media is described by Barwhale, et al., *Planta*, 167, pp. 473–481 (1986), but without the NAA hormone. The explants are plated on the agar surface by being laid on their side. The excised embryonic seed axis plated on the agar medium are incubated at 15° C. in the dark overnight.

(4) Exposing The Meristem

The washed seed axis explants are now ready for microdissection to expose the meristems of the seed axes. This dissection is performed under sterile distilled water and with sterile tools. The dissection consists of removing the embryonic leaf, or leaves if there is more than one, that obscure the meristem on each of the excised seed axes. The fully dissected explants are transferred to another petri dish containing sterile distilled water.

(5) Pre-Blast Hormone Treatment

After all the dissections are completed, the explants are again washed in three to five rinses of sterile distilled water. The free water is removed by pipette after the final rinse. The treated explants are then laid on their side on the surface of standard OR ccb medium made with fresh BAP but not NAA. The explants are incubated overnight, or for 24 hours maximum, at 15° C. in the dark. The treated excised embryonic axes with exposed meristems are now ready for the accelerated particle transformation blast.

(6) Genetic Material And Carrier Particle Preparation

Ten milligrams of amorphous crystalline gold powder, or of an equal mixture of 1–3 micron gold spheres and crystalline gold powder is measured into the bottom of a 1.5 ml Eppendorf microfuge tube. Care is taken to ensure that the gold did not spill on the sides of the tube, since that would make it difficult to resuspend the gold due to the small volumes used in the preparation process. 100 μl of 0.1M spermidine (free base) is added to this microfuge tube and the microfuge tube is vortexed well. 1 to 20.0 μg of double-stranded DNA is then added to the microfuge tube and the tube is then vortexed gently but completely. While the DNA/carrier particle mixture is gently vortexed, 100 μl of 2.5M $CaCl_2$ is added to the tube. The vortex is stopped, and precipitation is permitted for 10 minutes at room temperature. The preparation could be stored at this point for some time. Shortly before use, the mixture of DNA and carrier particles is given a brief spin in a microfuge. The cleared supernatant is removed completely, and the precipitant consisting of the DNA and carrier particles is resuspended in 20 ml of 100% ethanol. The resuspended DNA and carrier particle mixture is then sonicated in a water bath sonicator for two to three brief one second exposures. The resulting suspension is then coated onto the carrier sheet, at a calculated rate of 0.05 milligrams per square centimeter of the carrier sheet. After allowing the gold to settle, the excess ethanol is drained away and the sheet is dried. These preparations of DNA and carrier beads are made fresh daily.

(7) Blasting

At this point in the process, the carrier sheets are placed upon the apparatus for the blasting process. This procedure and apparatus are similar to that disclosed in U.S. Pat. No. 5,015,580, which is hereby incorporated by reference. The cotton explants are plated on 12% xanthan gum target plates. Using the normal germination and pre-blast hormone treatments described above, typically 25 explants are found to fit on each of the target surface within the blast area.

The parameters used for the particle-mediated transformation blast itself includes a relatively high electric discharge voltage through the gun, typically in the range of 15–25 kilovolts. The standard voltage used is 18KV. The voltage is adjusted to achieve a level of impact on the treated axes such that the rate of survival of the meristems is between 40% and 90%. In other words, the blast force is adjusted to a level such that at least some of the meristems are rendered non-viable by the process. The blasting experiments are conducted at 350 milliliters of mercury, with helium introduced at a rate of 1.5 liters per minute at atmospheric levels, and approximately 5.0 liters per minute under the vacuum.

Each of the target tissues is blasted once or twice during the same day. Target tissues blasted twice in the same day are blasted once in the morning and once in the afternoon, with the explants stored between successive blasting procedures in a moist chamber at approximately 28° C. in the dark. The target tissues are placed in the dark immediately after each blasting exposure.

(8) Post-Blast Protocol

The explants are now removed from the target surface, and plated in a normal orientation on OR ccb medium made with fresh BAP but no NAA. Care is taken not to expose the explants to excessive light. Care is taken to keep the meristem from contact with any media, and no wet plates are utilized. The fresh explants are plated and then incubated at 28° C. in the dark for one to two full days.

One day after the blasting, a preliminary assessment of transient enzyme activity is conducted on the resultant tissues. The assay is conducted at this time to check for the quality of the bead preparation protocol, and also to look specifically at the number of transformation events in the meristem, a rough approximation of which can be made by checking the transient activity of the explants at this stage. Although due to the heavy damage from the blasting process 20 to 60% of the meristems are sufficiently damaged so as to never produce shoot, those same damaged meristems will, upon assay, exhibit excellent transient gene activity particularly of the GUS gene using this procedure. Thus, the tissues can be assayed at this step for the percentage of GUS activity, even though shoots are not yet evident on the meristems subjected to the procedure.

Following the initial post-blast incubation on the medium described above, the cotton explants are transferred to the dextrose-based woody plant medium (WPM), minus BAP plus carbenicillin and benomyl, in plantcons again under low light. The WPM medium mixture, based on Lloyd and McCown, *Proc. International Plant Propagation Soc.*, 30:421–427 (1981) is prepared as follows: $NH_4NO_3$ (400 mg/L), $Ca(NO_3)_2 \cdot 4HOH$ (556 mg/L), $K_2SO_4$ (990 mg/L), $CaCl_2 \cdot 2HOH$ (96 mg/L), $KH_2PO_4$ (170 mg/L), $H_3BO_3$ (6.2 mg/L), $Na_2MoO_4 \cdot 2HOH$ (0.25 mg/L), $ZnSO_4 \cdot 7HOH$ (8.6 mg/L), $CuSO_4 \cdot 5HOH$ (0.025 mg/L), $FeSO_4 \cdot 7HOH$ (27.8 mg/L), $Na_2EDTA$ (37.3 mg/L), Thiamine·HCL (1.0 mg/L), Nicotonic acid (0.5 mg/L), Pyridoxine·HCl (0.5 mg/L), Glycine (2.0 mg/L), Myo-inositol (100 mg/L), Dextrose (20 g/L), Agar (3.0 g/L), Gelrite (1.1 g/L), Calcium gluconate (1.29 g/L), Carbencillin (200 mg/L) and Benomyl (60 mg/L). The tissues are incubated at 28° C. in the dark for one to seven days.

Following the culturing steps outlined above, the plantcons are then moved to full light exposure so as to induce shoot development in the tissues under cultivation.

(9) Identification of Transformant Events

The plantcons are then moved to a cultivation chamber and exposed to 16 hour light periods at 28° C. A number of cultured explants then proceed to exhibit shoot elongation and development from the plated tissues. It then becomes necessary to evaluate the growing shoots to ascertain the level of germ-line transformation events which are achieved through this process. The assay procedure is conducted at such a point that the shoots each have developed their first leaves. The outermost one-third to one-half of each leaf is then cut off completely across the leaf through the midrib. The leaves are then assayed for GUS activity to identify GUS-positive plants.

At this point, the quality of the event is characterized depending on the level of GUS activity in the leaf. Some of the leaves exhibited only uneven or irregular GUS expression, indicating chimeric plants. Based on the results below and experience with other plant systems, we have observed and verified that a transformation of the vascular system, as exemplified by the leaf petiole, correlates very well with the occurrence of a germline transformation event. Some of the leaves seemed to be totally blue, indicating putatively clonal transgenic plants. If the plant is characterized as germline transformed, the plant is transferred into rooting conditions and grown out in the greenhouse. For chimeric plants, the plant is pruned to just above the transformed leaf so as to force the axillary bud to grow from the transformed area of the plant after which it is retested.

For plants that tested negative, the leaves are removed, and the plants are cultured until newly formed leaves are regenerated. Tests are again conducted. This process is repeated three times before a final negative determination for the plants is made.

The entire process as described above, from initial plating of the seeds to the recovery of an initial generation transgenic plant requires approximately three to five weeks. Based on the initial results as described above, we expect that approximately one mericlonal transgenic plant will occur per approximately 100 to 500 meristems exposed to the blasting process. Of the mericlonal plants produced from the process, approximately 0.1–1.0% will be found to have transformed germ lines. Thus, although the yield may seem low, this process allows for the relatively rapid and more inexpensive generation of large numbers of transgenic plants than other procedures because the process can be performed quickly. The transgenic plants will transmit the inserted genes by Mendelian inheritance, and the process can be performed directly on elite cotton lines, even Sea Island and Pima lines, which are resistant to tissue-culture methods.

(10) Examination of Fiber

After obtaining a transgenic plant, one must examine the plant fiber for peroxidase expression and altered characteristics. The examples below disclose various methods of examining the fiber for peroxidase expression. This section discloses various ways of measuring fiber characteristics.

1. Strength

Fiber strength is an important factor in determining yarn strength. Fiber with superior strength is preferred in the manufacturing process. Cotton fiber strength can be measured in a number of ways. The most common measurement is that of the fiber bundle strength.

Fiber bundle strength measurements are preferably made with a ⅛ inch spacer between the clamp jaws (⅛ inch gauge) of Stelometer or the Motion Control High Volume Instrument (HVI) and the results are given in grams per tex. A tex unit is equal to the weight in grams of 1,000 meters of the material. Results of Stelometer ⅛ inch gauge tests are calculated by the use of the following formula. The results are adjusted to Pressley level by the use of calibration cottons. Typical cotton fiber strength is given in Table 1.

$$\text{Grams per } tex \text{ (g/tex)} = \frac{\text{breaking load (kg)} \times 15}{\text{bundle weight (mg)}}$$

2. Length

There is a wide range of fiber lengths within a bale of cotton. Comb sorters provide a way of sorting the fibers into different length groups, usually ¹⁄₁₆ of inch intervals. Instruments such as a fibrograph and HVI system can be used to compute length in terms of "Mean" and "Upper Half Mean" length. The mean is the average length of all fibers and the upper half mean (UHM) is the average length of longer half of the fiber distribution. The fibrograph measures length in span lengths at a given percentage point. For example, the 2.5% span length is the span length that agrees best with classers staple and indicates that 2.5% of the fibers are of this length or longer.

3. Micronaire

Fiber fineness and maturity in combination can be determined by the micronaire test. This is an instrument test which measures the resistance of a plug of cotton to air flow. From 47 to 52 grains of cotton are placed in the instrument specimen holder and compressed to a fixed volume. Air at a known pressure is forced through the specimen, and the amount of flow is indicated by a direct reading scale. The readings obtained are a relative measurement of either the weight per unit length or cross-sectional size of the fibers. Because the instrument measurements may differ from the actual weight per inch, depending up on the fiber characteristics of the sample, the results are reported in terms of "micronaire reading" instead of micrograms per inch. The air flow reacts to the surface area of the fibers presented to it. Because both small diameter mature fiber and a large diameter thin walled fiber will present a relatively high surface area, the test will indicate both maturity and fineness. The fiber diameter within a given variety of cotton is fairly consistent. Therefore the micronaire index will more likely indicate maturity variation than variations in fineness. Typical micronaire readings for fiber are given in Table 1.

4. Maturity

Cotton fiber maturity is described as the total cell wall thickness related to the diameter or width of the fiber. A mature fiber is defined as one in which twice the cellulose wall thickness equals or exceeds the width of the lumen.

5. Arealometer

An arealometer is an air flow instrument responsive to specific area and immaturity ratio. Hence, it has been used to measure cotton fineness and immaturity. Specific area (A) is defined as the ratio of the external surface of the fibers to the volume of fibrous material; and immaturity ratio (I) is defined as the area of a circle having the same perimeter as an average fiber to the actual cross section area of the fiber (Hertel and Craven, Textile Research J.21:765–774, 1951). Other parameters calculated or measured by arealometer include perimeter (p), weight fineness in terms of area density of cellulose (W), and wall thickness (t). The increase in apparent specific area produced by compression in Arealometer (D) is related to $I^2$.

6. Variation in Fiber Properties

Cotton fibers from the same plant show variations in properties depending on the boll positions on the plant. For example the bolls nearest to the main stem (inner bolls) show much more uniformity in their strength, length and micronaire measurements compared to the bolls farthest on branches. Also there are variations in fiber properties of plants from the same cultivar. Because of these variations, we established a base line and magnitude of natural variation in fiber properties of the inner boll fibers of cotton plants grown under similar conditions. A large number of cotton plants were grown in the greenhouse and fibers from inner bolls were collected and fiber properties measured. These measurements are tabulated below in Table 1. Table 1 shows the variation that we can expect for each cultivar. Therefore, any changes within that magnitude in transgenic fibers may not be significant.

TABLE I

| | | Fiber Properties* of Cotton Cultivars | | | | | | | | |
|---|---|---|---|---|---|---|---|---|---|---|
| | | Strength (gm/tex) | | | Length (inches) | | | Micronaire | | |
| Variety | #Plants | Ave. St. (SD) | Max. | Min. | Ave. (SD) | Max. | Min. | Average (SD) | Max. | Min. |
| DP 50[1] | 35 | 18.9 (0.834) | 20.6 | 17.5 | 1.157 (0.037) | 1.24 | 1.10 | 4.005 (0.396) | 4.8 | 3.0 |
| DP 90[1] | 35 | 21.84 (0.892) | 23.6 | 19.9 | 1.145 (0.04) | 1.21 | 1.07 | 3.926 (0.269) | 4.6 | 3.5 |
| C 312[1] | 20 | 19.490 (0.527) | 20.9 | 18.7 | 1.192 (0.030) | 1.22 | 1.12 | 3.87 (0.429) | 4.7 | 3.2 |
| Pima[2] | 30 | 26.817 (1.299) | 29.5 | 23.6 | 1.214 (0.039) | 1.31 | 1.15 | 3.553 (0.235) | 3.8 | 2.9 |
| Sea Island[2] | 8 | 27.763 (1.80) | 30.9 | 24.3 | 1.459 (0.079) | 1.62 | 1.36 | 2.913 (0.127) | 3.0 | 2.7 |

*All are stelometer data of inner boll fibers grown under similar conditions.
SD = standard deviation.
[1] = upland varieties
[2] = barbadense varieties

EXAMPLES

A. E6-3B Promoter

Plasmid pSKSIE6-3B contains the promoter of fiber-specific gene E6-3B. We have demonstrated that a 2.7 kb Sal (Mbo I)/Nco I fragment contains a functional promoter by linking the promoter to a marker gene, GUS, and observing transient expression. Subsequently, we have generated stable transgenic cotton plants using this promoter upstream from a carrot extensin gene and demonstrated that the extensin gene was expressed in a tissue-specific and developmentally regulated fashion in cotton fibers (John and Crow, *Proc. Natl. Acad. Sci.*, 89:5769–5773, 1992).

Next to the unique Nco site in the E6-3B promoter is a Bst XI site. In order to construct a promoter fragment for peroxidase gene expression, we removed the Nco site. For this removal, the plasmid was digested with Bst XI and the ends repaired by treatment with T4 polymerase. This procedure destroyed the Nco site, and the resulting ends were blunt. We added Sal I linkers to the fragment (2.7kb). After digestion with Sal I and gel purification, this fragment was then ligated to the Xho I site of SK+ vector. Clones containing the promoter in both orientations were identified by Sekar SDS-gel electrophoresis and subsequent plasmid analysis by restriction mapping and sequencing.

A clone designated as E6-3B/Sac will have the promoter in such an orientation that when the coding region of a gene is ligated at any site between Sal I and Sac I in the SK vector, transcription will be towards the Sac I site. Similarly, when a clone is designated as E6-3B/Kpn the promoter is such an orientation that the transcription is towards the Kpn site. Thus, genes can now be ligated to a number of restriction sites downstream from the promoter.

In addition to the two vectors described above, we modified the SK+plasmid to include either an Nde or an Nhe restriction site at a unique Nae site in the fi phage intergenic region. This was done to create a new unique site for inserting marker genes. The Nae I site is about 340 bp away from the Sal/Xho sites where the E6 promoter is inserted. The SK+ vector was digested with Nae and phosphorylated Nde or Nhe linkers were ligated to the Nae site. The protocol for addition of linkers is well established and is described in *Current Protocols in Molecular Biology* (supra). This procedure resulted in two modified vectors, one containing a unique Nde site and the other containing an Nhe site. However, addition of these sites may have disabled the single-strand-forming ability of these phagemids.

These two vectors were digested with Xho I and the E6-3B promoter fragment was ligated into this site. These constructions resulted in E6-3B/Sac and E6-3B/Kpn plasmids and have the additional property of having unique sites away from the cloning sites for marker gene addition.

B. B8 Promoter

We have characterized a fiber-specific promoter from pSKSIB8-HI. A 2.2 kb Bam HI/Bst BI fragment contained a functional promoter by transient expression analysis of the GUS gene. The promoter was modified to include two restriction sites at the 3'-end next to a unique Bst BI site for convenient cloning. The Bst BI site is 120 bp from the putative initiation codon of B8 gene. We replaced the 120 bp region with a DNA fragment that contained an Eco RI and Bam HI sites. This was accomplished by PCR using primers MEJ 117 and MEJ 282. The sequences of these primers are presented in SEQ ID NOs: 7 and 8.

A plasmid containing the B8 promoter and a GUS marker gene, pSKB8-GUS was digested with Bst BI and Eco RI and a 5.2 kb fragment was gel-purified. The PCR product was similarly digested with BstBI and Eco RI and ligated to the 5.2 kb fragment. The promoter can be excised as a Bam HI or Xba/Eco RI fragment. Furthermore, the Bam HI fragment was blunt-ended and Sal I linkers were added. The Sal fragment was then ligated to the Xho I site of SK vector and clones containing the promoter in different orientations were selected. When the transcription is towards Sac I site, the B8 promoter is designated as B8/Sac, whereas when it is towards Kpn site it is designated as B8/Kpn.

C. Cloning of 3' Untranslated Region and Poly-(A) Addition Signal

Functional genes contain a 3' untranslated region next to the coding region. This region contains the stop signal for the end of transcription. In addition, the 3' untranslated region may also influence the translation or stability of the transcripts.

In order to provide a 3' untranslated region to the peroxidase genes, we cloned a DNA fragment from the 3'-end of the fiber gene E6-3B from clone pSKSIE6-3B using primers MEJ35 and MEJ36 (SEQ ID NOs: 9 and 10) and PCR amplification. The resulting DNA (313 bp) was digested with Hind III and Bam HI and cloned into SK+ vector. The poly (A) addition signal from nopaline synthase was added as a Bam HI/Xba I fragment. (See FIG. 4C)

Furthermore, in order to facilitate gene cloning, we made two other constructs containing the E6-3B 3'-end along with the NOS A sequence as a single fragment. For these constructs, the E6-3B 3'-end and the NOS A sequence were excised as a single fragment by Hind III/Xba. The ends were repaired by T4 polymerase. Not I linkers were added and cloned into an SK+ vector at the Not I site. (See FIG. 4A) A third fragment was cloned after PCR amplification using primers MEJ 207 (SEQ ID NO: 11) and DR112 (SEQ ID NO: 12). The PCR product was cloned into the SK+ vector. The 3'-end sequence can now be excised from these three plasmids by a number of restriction sites as required for various cloning strategies. (See FIG. 4B) In the description of the cloning, the NOS A poly(A)-addition signal along with the E6-3B 3'-end will be referred to as the "3'-end".

D. Cloning of Peroxidase Genes

1. In General

Figure 5:
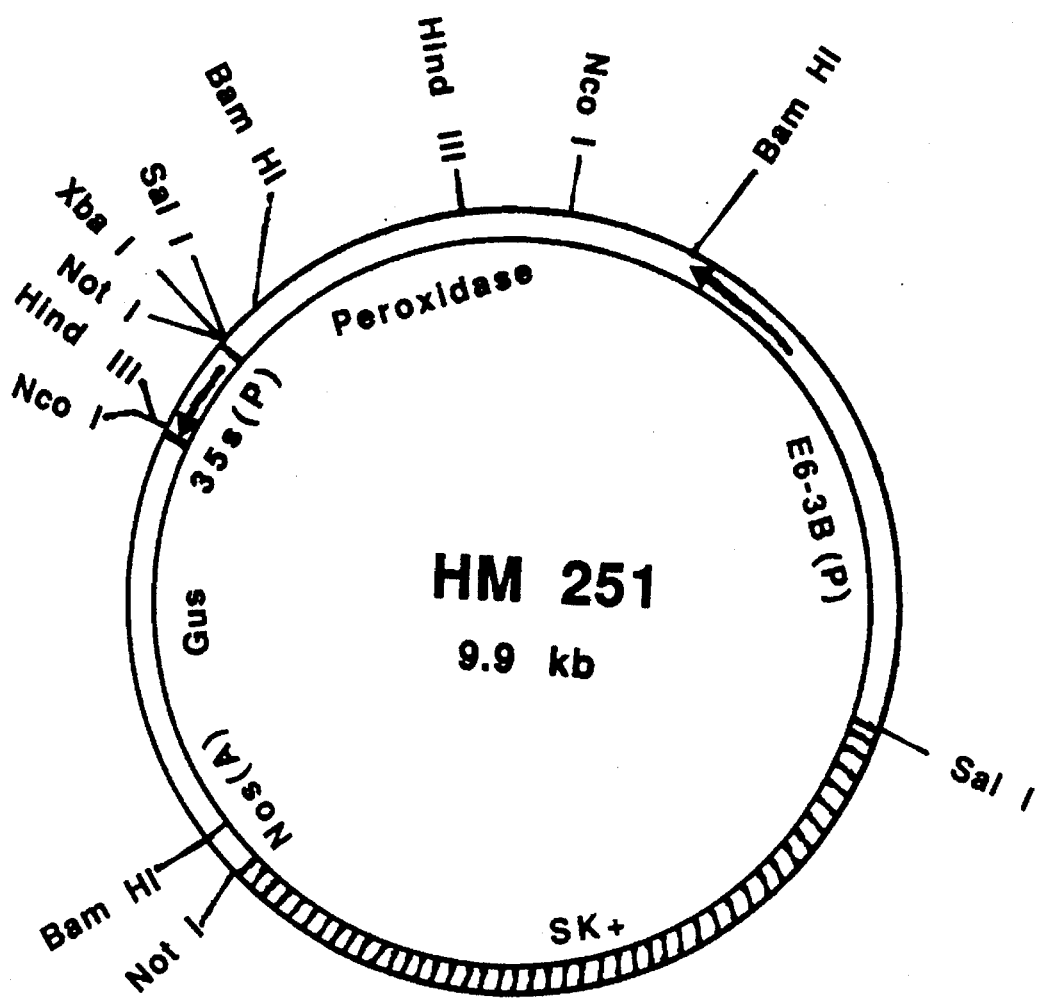
FIG. 5 is a diagram of HM 251.
Figure 6:
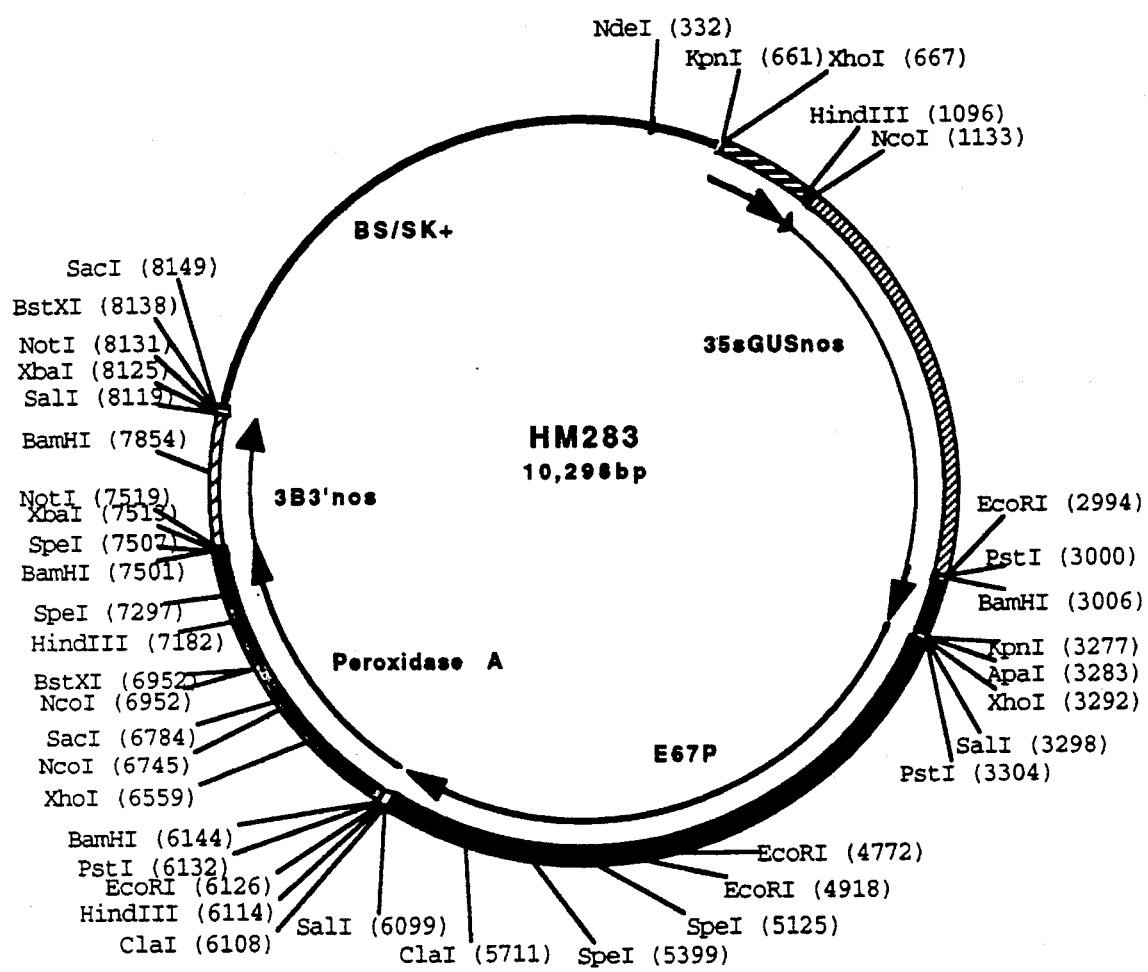
FIG. 6 is a diagram of HM 283.
Figure 7:
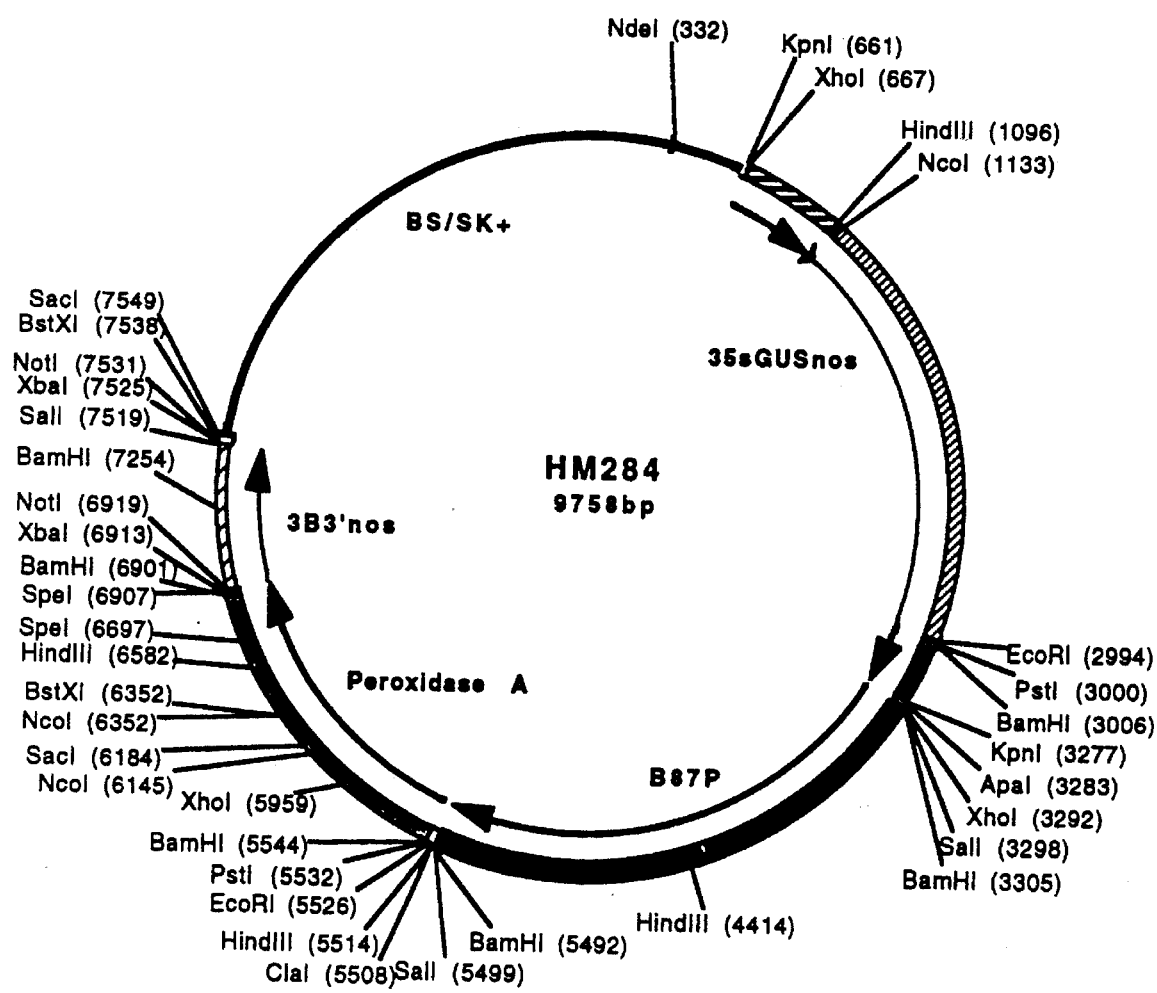
FIG. 7 is a diagram of HM 284.

The peroxidase gene is inserted into a transformation vector in such a fashion that when integrated into cotton genome, the peroxidase is expressed preferentially in fiber cells. This is accomplished by fusing a fiber specific promoter to the coding region of the peroxidase gene. In addition the gene is provided with a transcription termination signal to stop transcription. Typically, included in the vector is a marker gene to follow the transformation of the plant tissue. The description of various cotton transformation vectors containing peroxidase genes, HM 251, HM 283 and HM 284 are given in FIGS. 5, 6 and 7.

2. Construction of HM 251

A 271 bp NOS (A) Bam HI/Xba fragment was gel-purified from plasmid 2117 and inserted into SKE6-3B plasmid at Bam HI/Xba sites. The resulting plasmid was then identified by sekar gel electrophoresis (plasmid A). The cationic peroxidase gene-containing plasmid GrmM-E39 was obtained and digested with Eco RI. The sequence of this gene is reported in D. Ritter, *Plant Physiol.*, 102:1351, 1993. (This article is hereby incorporated by reference as if fully set forth herein.) Bam HI linkers were added. The insert (1.3 kb) was then gel-purified and ligated into Bam HI linearized plasmid A. The orientation of the insert with respect to the promoter was determined by restriction digestion analysis. If the orientation of the insert is in such a way that when the gene is transcribed an RNA for peroxidase enzyme is produced (sense) then the construct is HM 251. A beta-glucuronidase marker gene (2.7 kb) was then inserted into HM 251 at Not I site.

If one wishes to reconstruct the GrmM-E39 sequence, the published sequence of this cotton cationic peroxidase gene may be used to construct probes capable of hybridizing to the sequence in either a cotton cDNA or genomic library. Standard molecular biology techniques may be used to create these clones and libraries.

3. Construction of HM 283

We made two additional constructs using the insert of GrmM-E39. In construct HM 283, a modified version of E6-3B promoter was used, and in HM 284 a B8 promoter was used. E6-3B promoter contains a unique Nco I site. This Nco site is the site of translation initiation in E6 gene. This Nco site is preserved in the construct HM 251.

The insert of GrmM-E39 contains its own initiation codon. In order to avoid the presence of an ATG codon at the 5'-end before the ATG codon of the peroxidase gene, we deleted the Nco I site of E6 promoter as follows: Flanking the Nco site is Bst XI site. The plasmid was digested with Bst XI and then treated with polymerase T4. This procedure destroyed the Nco site. Sal I linkers were then added and the modified promoter fragment gel-purified. The fragment was ligated into the Xho I site of SK+ vector and the orientation of the promoter was determined. The modified E6 promoter, E6-3B-7P, was then used in the construction of HM 283. The Bam HI fragment of GrmM-E39 was ligated to the Bam HI site of E6-3B and orientation determined by restriction analysis. A NOS (A) fragment was then added at Xba I site.

The marker gene GUS was added as a Kpn I fragment at the Kpn I site to complete the construction.

4. Construction of HM 284

HM 284 was constructed as follows: A 2.2 kb Bam HI fragment containing the promoter was isolated from a fiber specific gene EMBLSI-B8 and cloned into the Bam HI site of SK+ vector. The orientation of the insert was determined by restriction analysis. The peroxidase insert from E6-3B-7P was excised as a Cla/Xba fragment and cloned into the Cla/Xba site of B8 promoter vector. The GUS marker gene was then added as a Kpn fragment.

5. Identification of Tobacco and Arabidopsis Peroxidase Genes a. Anionic Tobacco Peroxidase Genes A tobacco cDNA library was obtained from Clonetech Laboratories, Inc., Calif.. The mRNA source for the library was *Nicotiana tabacum*, cv. Xanthi-nc, 30-day post emergence seedlings grown in 16 hrs light/8 hrs. darkness per day. The cDNA was cloned into lambda gt11 5'-Stretch vector. The library was propagated and screened according to the instructions of Clonetech Labs.

For screening peroxidase genes, we generated two probes from published sequences. Lagrimini, et al. described a lignin-forming peroxidase from tobacco, *Proc. Natl. Acad. Sci. USA*, 84:7542–4546, 1987. Two PCR primers were synthesized to amplify a DNA fragment based on this nucleotide sequence. The primers were MEJ 342 (SEQ ID NO: 13) and MEJ344 (SEQ ID NO: 14).

PCR amplification from stem poly(A) RNA of tobacco resulted in a 550 bp fragment. We used this fragment to probe the tobacco cDNA library and identified one phage that strongly hybridized to the probe. The insert in the phage was then subcloned into the ECO RI site of SK vector to create Tpa-1. The sequence of the Tpa-1 insert is presented in SEQ ID NO: 15.

We isolated a second peroxidase gene from tobacco based on the sequence published by Diaz-De-Leon, et al. (*Plant Physiol.*, 101:1117–1118, 1993). Four PCR primers were synthesized, MEJ 350, MEJ 351, MEJ 352, and MEJ 353 (SEQ ID NOs: 16, 17, 18, and 19). MEJ 350 and 351 were used for PCR amplification from the genomic DNA of tobacco to generate a 480 bp fragment. Similarly, MEJ 352 and 353 were used to generate a 250 bp fragment. The mixture of these two fragments was then used as a probe to screen the tobacco cDNA library. This screen resulted in one phage. The phage insert was subcloned into SK vector to generate plasmid Tpa-2. The nucleotide sequence of Tpa-2 is presented in SEQ ID NO: 20.

Tpa-1 and Tpa-2 share extensive homology (97.5% similarity) in a 200 bp region. The molecules are very different at other regions. The heterologous region can be used as a probe to isolate a full length cDNA clone from the tobacco library. Thus, it appears that Tap-2 is a very different peroxidase than Tpa-1 or the published tobacco peroxidase (Lagrimini, et al., supra).

b. Isolation of Full-length Tpa-1 and Tpa-2 Genes

Comparison of nucleotide sequences of Tpa-1 and Tpa-2 and northern analysis showed that the clones were partial cDNA sequences. In order to express these genes in cotton, full-length genes were obtained as follows: We used PCR to amplify the 5'-end of Tpa-1 from the poly(A) RNA of tobacco stem. Two PCR primers were synthesized, MEJ 423 and MEJ 424 (SEQ ID NOs: 21 and 22). Amplification resulted in a 451 bp fragment. This fragment contains an internal Sca I site. Tpa-1 also contains an internal Sca I site. We will use this Sca I site to join the cDNA and PCR product. The PCR product was sequenced to confirm proper maintenance of reading frame. The resulting full-length gene sequence is shown in SEQ ID NO: 23.

The PCR amplified fragment overlaps with the Tpa-1 sequence at the 5'-end. However, the 216 base overlapping region contains 18 nucleotide substitutions. Thus, it appears that the PCR amplification may have occurred from a slightly different peroxidase RNA population than Tpa-1. Fusion of the PCR product and the Tpa-1 at the common Sca-1 site would result in a 1270 bp gene (Tpa-1L) and would code for a 324 amino acid protein. When the predicted amino acid sequence of Tpa-1L was compared to the tobacco peroxidase, extensive homology (97.8% similarity) was found. There are 12 amino acid differences between the two peroxidases. Thus, the tobacco peroxidase gene identified by Lagrimini, et al., supra is different than the one we have isolated.

c. Arabidopsis Peroxidase Gene Isolation

We screened an *Arabidopsis* cDNA library using the tobacco Tpa 1 cDNA as a probe. The cDNA library was obtained from Clonetech Laboratories. The library was constructed in Lambda gt11 vector using 4.5 week old seedlings as a source of mRNA. The screen resulted in six strongly hybridizing phages. The inserts of these phages are being subcloned. Two of the phages, Apc-1 and Apc-2 contained inserts of 1.2 kb in length.

E. Plant Transformation

The following plasmids were introduced into cotton seed axis and transgenic plants were generated: 1) HM 251, 2) HM 283, and 3) HM 284. Transgenic plants containing HM 251 were screened for GUS activity and fibers from transformants were tested for fiber properties.

We have established successful particle bombardment-mediated cotton transformation parameters. We have generated transgenic plants containing genes for carrot extensin (a hydroxy proline-rich cell wall protein); parathion hydrolase (a bacterial enzyme capable of removal of coumapos from waste water), a number of cotton antisense fiber-specific genes, Kapok fiber genes, bacterial bioplastic genes, and plant hormone genes. In each of these cases the proteins have been expressed in a fiber-specific manner. Thus, validation of the transformation protocol, construction of cotton expression vectors, as well as specificity of fiber promoters have been achieved.

The protocol for the generation of transgenic cotton developed by McCabe and Martinell (Bio/Technology, 11:596–598, 1993) allowed us to generate germ-line and non-germline (epidermal) transformants. In the germ-line transformants the transgene is passed on to progeny in a Mendelian fashion. With epidermal transformants, the progeny are not transgenic. Therefore the epidermal plant has to be propagated vegetatively (McCabe and Martinell, Bio/Technology, 11:596–598, 1993). However since cotton fiber is derived from maternal epidermal tissue, epidermal transgenic plants are suitable for testing the effect of transgenes on fiber modification. We have monitored the transgene expression of vegetatively propagated epidermal transformants over three years and have shown stable expression.

The frequency of generation of epidermal transformants is an order of magnitude higher than that of germline tranformants (McCabe and Martinell, supra). Thus, in a given experiment we generate a large number of epidermal transformants that can be used for fiber modification studies.

F. Analysis of Transgenic Plants

Genetic construct HM 251 was introduced into DP-50 cotton seed axis by particle bombardment, as described above, and transgenic plants were generated. We analyzed fibers from 19 transgenic plants for any changes in their fiber properties. The stelometer results are shown below in Table 2. There are three plants, 17-08340, 17-08802, and 17-08917 that show 15% or more increase in strength. Transgenic plant 17-08802 show 62% increased strength compared to control DP-50 fibers.

TABLE 2

Transgenic Fiber Analysis of HM 251 Plants*

| # Plant | Epidermal | Germ line | Strength gm/tex | Length (inches) | Micronaire |
|---|---|---|---|---|---|
| 17-07525 | yes | — | 18.3 | 1.18 | 3.6 |
| 17-07527 | yes | — | 17.7 | 1.16 | 3.5 |
| 17-08014 | yes | — | 18.8 | 1.11 | 4.1 |
| 17-08110 | yes | — | 17.8 | 1.18 | 3.7 |
| 17-08334 | yes | — | 17.7 | 1.19 | 3.7 |
| 17-08339 | yes | — | 18.2 | 1.12 | 4.0 |
| 17-08340 | yes | — | 21.7 | 1.17 | 4.5 |
| 17-08519 | yes | — | 16.7 | 1.17 | 4.0 |
| 17-08802 | yes | — | 29.9 | 1.08 | 3.7 |
| 17-08803 | yes | — | 18.5 | 1.10 | 3.5 |
| 17-08811 | yes | — | 18.3 | 0.96 | 4.4 |
| 17-08812 | yes | — | 14.5 | 1.12 | 3.6 |
| 17-08814 | yes | — | 17.3 | 1.15 | 4.0 |
| 17-08827 | yes | — | 18.1 | 1.14 | 3.7 |
| 17-08912 | — | yes | 18.8 | 1.07 | 4.7 |
| 17-08913 | yes | — | 19.1 | 1.17 | 4.9 |
| 17-08914 | yes | — | 16.8 | 1.06 | 3.2 |
| 17-08915 | yes | — | 17.1 | 1.14 | 3.2 |
| 17-08917 | yes | — | 22.1 | 1.18 | 3.6 |
| DP-50 control | — | — | 18.4 | 1.17 | 3.7 |

*Stelometer data

It is our experience that usually only one out of every five transgenic plants expresses the transgene in appreciable amounts. Therefore, it is likely that of the 19 transgenic plants containing construct HM 251, only three or four may be expressing the peroxidase gene in appreciable amounts.

Because of the superior strength of 17-08802 fibers, we decided to limit further studies to only this plant and its fibers. We refer to the fibers of plant 17-08802 as #8802 fibers in subsequent discussions.

The inner, outer and mixed fibers of this plant were tested for fiber properties and the results are shown below in Table 3. The strength increase is found in fibers of all boll positions.

TABLE 3

Analysis of #17-08802 fiber*

|  | Inner | Outer | Mixed |
|---|---|---|---|
| Fiber Strength (gm/tex) | 28.5 | 29.9 | 28.2 |
|  | (18.9) | (17.5) | (17.6) |
| Length (inches) | 1.10 | 1.12 | 1.09 |
|  | (1.19) | (1.16) | (1.15) |
| Micronaire | 3.7 | 3.7 | 3.7 |
|  | (3.5) | (3.7) | (4.1) |

Numbers in the brackets are for control nontransgenic fibers.
*Stelometer data.
"Inner and Outer" refer to the position of bolls in the plant. When fibers from inner and outer bolls are mixed it is referred to a "Mixed".

In order to investigate whether the GrmM-E39 gene is over-expressed in 8802 compared to control DP-50 plants, we did a northern blot analysis. Poly(A) RNA was isolated from 10 and 15 day fibers of DP-50 and #8802 fibers and blotted to nitrocellulose filters after size fractionation in agarose/formaldehyde gels. The insert of GrmM-E39 was then hybridized to nitrocellulose. The results showed the #8802 fibers contained 5- to 10-fold more GrmM-E39 transcripts than control DP-50 fibers at 15 day. Additionally, the size of the hybridizing transcript in #8802 was about 300 bases more than that of control DP-50 plants. In our genetic construct HM 251, we have a 35 bp 5' untranslated region and a 271 bp NOS poly (A) added to the peroxidase gene. Thus, transcription from this gene is expected to produce an mRNA with 300 more bases.

Figure 8:
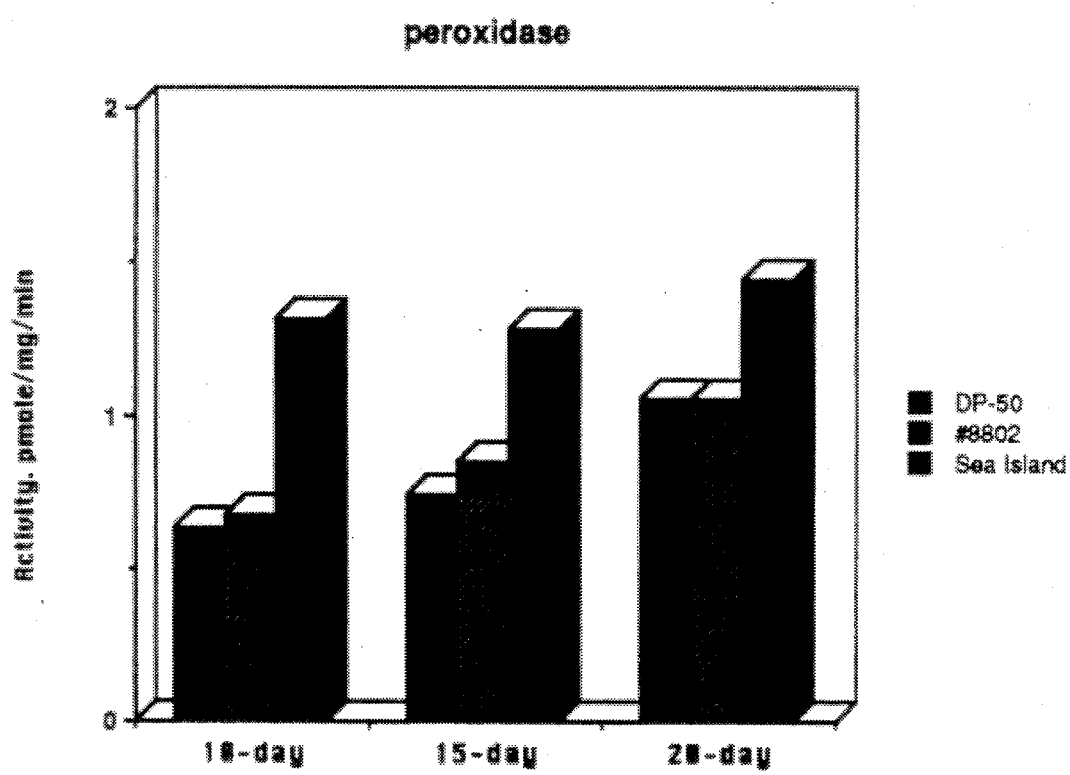
FIG. 8 is a bar graph of peroxidase levels in control DP-50, trangenic (#8802) and control Sea Island cotton.

To confirm that the increased transcripts levels resulted in increased levels of enzyme, a peroxidase activity was assayed in 0.28% guaiacol as described by Lagrimini and Rothstein (*Plant Physiol.*, 84:438–442, 1987). The results are shown in FIG. 8. There is no significant difference in the peroxidase activities of #8802 and DP-50 fibers at 10 and 20 days. However, there is an increase at 15 day. The increase in peroxidase activity at 15 day fiber of #8802 occurs during the optimal activity of E6 promoter, 15 through 20 days during fiber development (John and Crow, *Proc. Natl. Acad. Sci. USA*, 89:5769–5773, 1992). Interestingly, Sea Island fibers show significantly increased peroxidase activity in 10, 15 and 20 day fibers. Sea Island fibers are far superior in fiber strength. (See Table 1).

Since peroxidase enzymes are implicated in the plant hormone 3-acetic acid oxidation (Hinnman and Lang, *Biochemistry*, 4:144–158, 1965) we measured the IAA and ABA levels in fiber cells of #8802 and control DP-50 fibers with the help of Iowa State University, Department of Botany. The results showed that at 10, 15, 20 and 25 day the levels of IAA and ABA were similar to those of control fibers. This result suggests that the increased strength that we have observed in #8802 is not due to any significant variation of IAA or ABA levels.

Table 4, below, shows the bundle strength (Stelometer) of #8802 fiber in comparison with a number of upland and barbadense varieties of cotton. As seen from this table, #8802 fiber has similar strength as barbadense type (Pima and Sea Island) fibers. HVI tests also showed a 41% strength increase in #8802 fibers compared to DP-50 fibers. Arealometer data for DP-50 fiber is shown in Table 5 and shows that each of the parameters measured are within normal range.

TABLE 4

Comparison of Fiber Properties (Stelometer)

| | Strength (gm/tex) | Length (inches) | Micronaire |
|---|---|---|---|
| DP 90 | 21.83 ± 0.93 | 1.15 ± 0.040 | 3.85 ± 0.30 |
| DP 50 | 18.3 ± 0.83 | 1.16 ± 0.043 | 4.1 ± 0.40 |
| #8802* (DP 50) | 28.8 (28.3–29.9) | 1.12 (1.09)–1.13) | 3.67 (3.4–3.9) |
| Pima-S6 | 26.9 ± 1.3 | 1.22 ± 0.04 | 3.6 ± 0.24 |
| Sea Island | 27.8 ± 1.8 | 1.5 ± 0.08 | 2.9 ± 0.13 |

*Maximum and minimum observed data are given in brackets.

TABLE 5

Fiber Data Comparison (Arealometer)

| | DP 50 | 8802 | Pima |
|---|---|---|---|
| AH | 539 | 529 | 596 |
| A | 503 | 511 | 569 |
| D | 35 | 19 | 33 |
| IR | 1.86 | 1.51 | 1.83 |
| Maturity % | 80 | 93 | 81 |
| Perimeter | 47 | 37 | 41 |
| Weight Fineness | 3.6 | 2.81 | 2.81 |
| Wall Thickness | 2.4 | 2.51 | 2.13 |

Since the bundle strength can be affected by changes in the surface properties of fibers, we tested whether the strength profiles of individual fibers of #8802 have changed. For this fiber analysis, 200 individual fibers (Mantis test) were measured at North Carolina State University, Department of Textile and Apparel Management, College of Textiles. The summary of Mantis test data are shown below in Table 6. The breaking load for #8802 is increased, indicating increased strength, while the elongation at break is decreased for #8802. This may be due to the stiffness of the fiber wall. The test clearly showed that at the single fiber level there is significant increase in the strength of #8802 fiber. Thus Stelometer, HVI and Mantis tests confirm that the strength of #8802 fiber is superior to that of DP-50.

TABLE 6

Comparison of Single Fiber Data (Mantis Test)

| | DP 50 | 8802 |
|---|---|---|
| Breaking load [Tb (g)] | | |
| Average | 4.94 (2.4) | 8.11 (2.66) |
| Minimum | 0.70 | 1.47 |
| Maximum | 13.91 | 19.69 |
| Elongation (%) | | |
| Average | 19.46 (6.3) | 14.63 (3.7) |
| Minimum | 2.23 | 4.71 |
| Maximum | 49.43 | 24.3 |
| Work (uJ) | | |
| Average | 14.67 (7.9) | 16.34 (7.0) |
| Minimum | 0.29 | 2.06 |
| Maximum | 43.09 | 50.33 |

Standard deviation is given in brackets.

We also investigated whether increased fiber strength would be reflected in yarn made from #8802 fiber. For this determination, a miniature spinning test was conducted by International Center For Textile Research and Development, Lubbock, Tex. using #8802 fibers, as well as Pima and DP-50 fibers as controls. These results are shown below in Table 7. The #8802 yarn is 39% stronger than DP-50 yarn. Similar results were also independently obtained in spinning tests conducted by U.S. Department of Agriculture, Cotton Division, AMS, Clemson, S.C. 29631. Interestingly, this test not only showed significant (80%) increase in yarn strength but also showed that the number of neps present in #8802 fibers were five-fold less than control DP-50. Thin places in the fiber were down by 17-fold and thick places by 16-fold. These numbers suggest that the #8802 fiber is more uniform than the control DP-50 fiber.

TABLE 7

Miniature Spinning Text

| | Yarn Strength (lbs) |
|---|---|
| DP 50 | 121 |
| 8802 | 168 |
| Pima | 183 |

The yarn was then woven into fabric and tested for dye-binding characteristics along with fabric from control Pima and DP-50 fibers. Visual examination of fabrics showed no significant changes in the dye-binding properties between DP-50 and 8802. This was confirmed by colormeteric readings as shown in Table 8.

TABLE 8

Colorimetric Evaluation of Dyed Fabrics of DP50, #8802 and Pima

| Wave Length | OD #DP 50 | OD #8802 | OD Pima |
|---|---|---|---|
| 400 | 24.19 | 24.15 | 18.32 |
| 420 | 26.18 | 26.11 | 20.00 |
| 440 | 25.13 | 24.99 | 20.00 |
| 460 | 23.06 | 22.92 | 19.41 |

TABLE 8-continued

Colorimetric Evaluation of Dyed Fabrics of DP50, #8802 and Pima

| Wave Length | OD #DP 50 | OD #8802 | OD Pima |
|---|---|---|---|
| 480 | 19.79 | 19.79 | 17.58 |
| 500 | 16.63 | 16.65 | 15.35 |
| 520 | 12.39 | 12.42 | 11.98 |
| 540 | 9.45 | 9.50 | 9.46 |
| 560 | 7.36 | 7.40 | 7.53 |
| 580 | 6.06 | 6.10 | 6.32 |
| 600 | 5.75 | 5.82 | 6.06 |
| 620 | 6.35 | 6.43 | 6.68 |
| 640 | 7.24 | 7.47 | 7.69 |
| 660 | 10.36 | 10.73 | 10.96 |
| 680 | 18.28 | 18.54 | 18.75 |
| 700 | 29.49 | 29.30 | 29.10 |

G. Conclusion

Based on the physical property measurements described above, it is clear that the we have generated a cotton plant that has far superior fiber strength than the parent germplasm (DP-50). All other fiber properties of #8802 are within normal range. In greenhouse trials, the yield of #8802 is comparable with control DP-50 plants. Therefore we have not adversely affected other qualities of this fiber by increasing strength. The molecular data suggest that the increase in strength is due to increased peroxidase gene expression. We can rationalize the increased strength based on proposed functions of peroxidase enzymes in plant cells. Peroxidase are enzymes that catalyze cross-linking of various monomeric and polymeric cell wall components. Such cross-linking may help to stabilize the primary wall of fiber and hence increase its strength.

We have additional 25 plants in the green house that will provide fibers within the next two to three months. Additionally we have introduced the HM 283 construct into Pima variety and about 20 to 30 plants are expected within the next six months. Construct HM 284 is being introduced into both DP-50 and Pima. After confirmation of results, we intend to produce a number of germ-line transformants for field trails and eventual commercialization.

H. Additional Peroxidases

In addition to cotton cationic peroxidase, the following peroxidases were cloned and expressed in cotton: anionic peroxidases from Tobacco and horseradish and a cationic peroxidase from Arabidopsis.

1. Construction of Fiber Specific Vector for peroxidase expression.

An expression vector was constructed using a cotton fiber specific promoter E6 (John and Crow, *Proc. Natl. Acad. Sci.* 89:5769–5773, 1992). In order to increase the strength of the promoter we also added a cauliflower mosaic viral (35S) enhancer.

Figure 9:
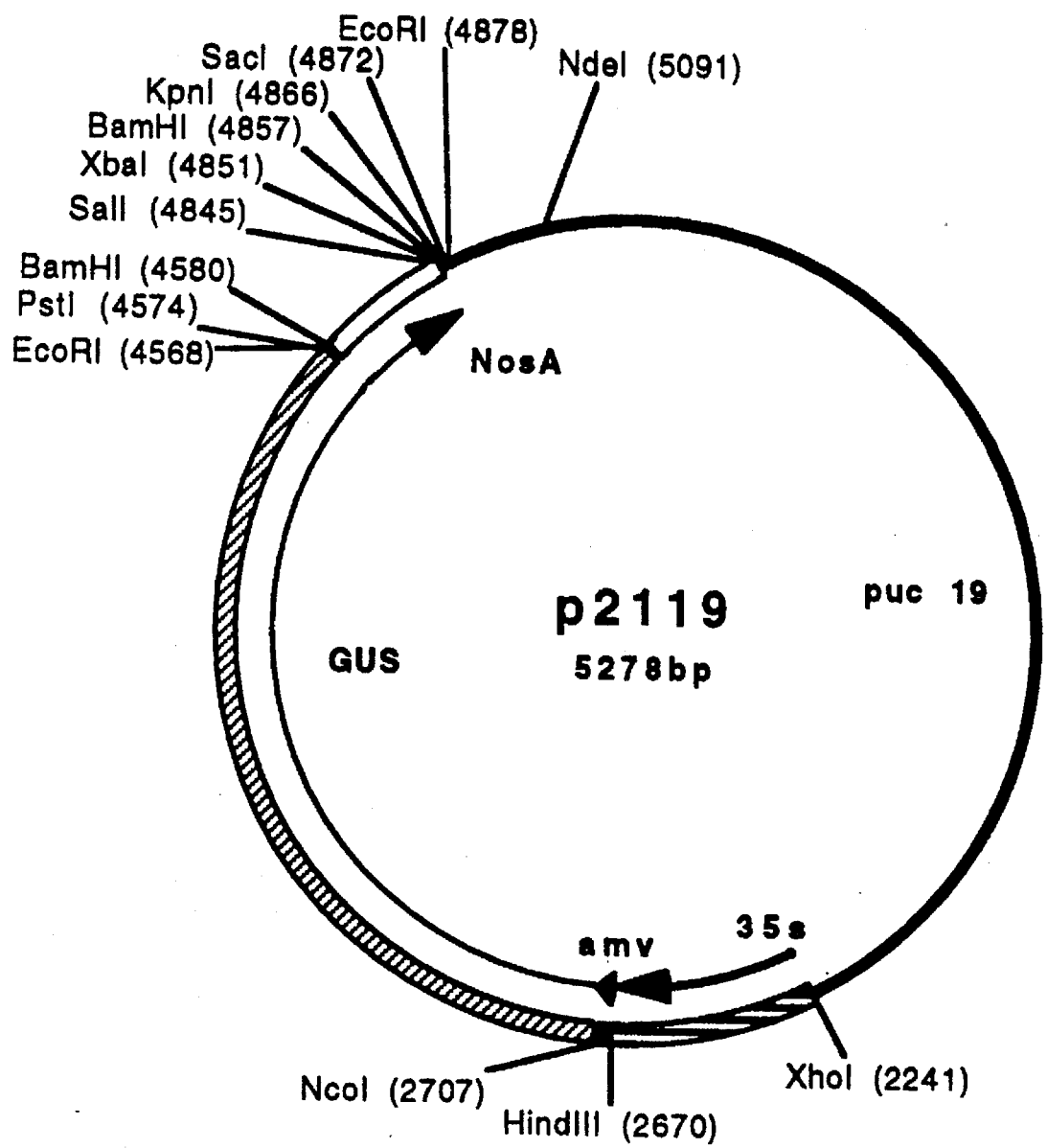
FIG. 9 is a diagram of p2119.

The 350 bp 35S enhancer from a previously constructed vector, p2119, was ligated as a Xho I/Eco RV fragment into a modified (Nae 1 site changed to Nde1) Bluescript SK+ vector (Stratagene) to generate pB844. The restriction map of p2119 is shown in FIG. 9. A 1200 bp E6 promoter fragment was then added at the EcoR-1 site of pB844 to generate pB903. The 1200 bp promoter fragment was isolated from pSKSIE6-3B (FIG. 1) by digestion with EcoR-1.

Figure 10A:
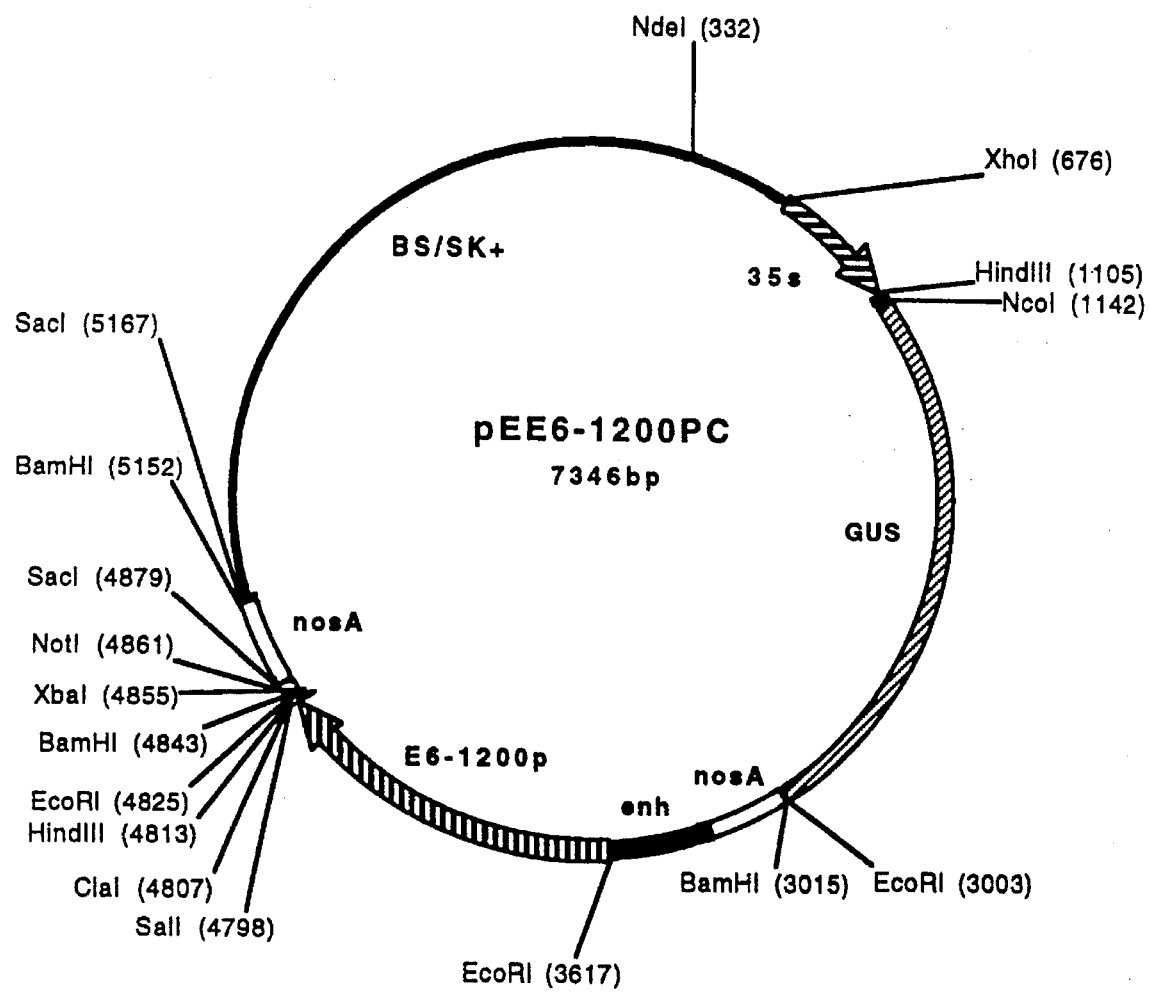
FIGS. 10A and B is a diagram of the restriction map of EE6-1200PC (FIG. 10A) and the construction of plasmid EE6-1200PC (FIG. 10B).
Figure 10B:
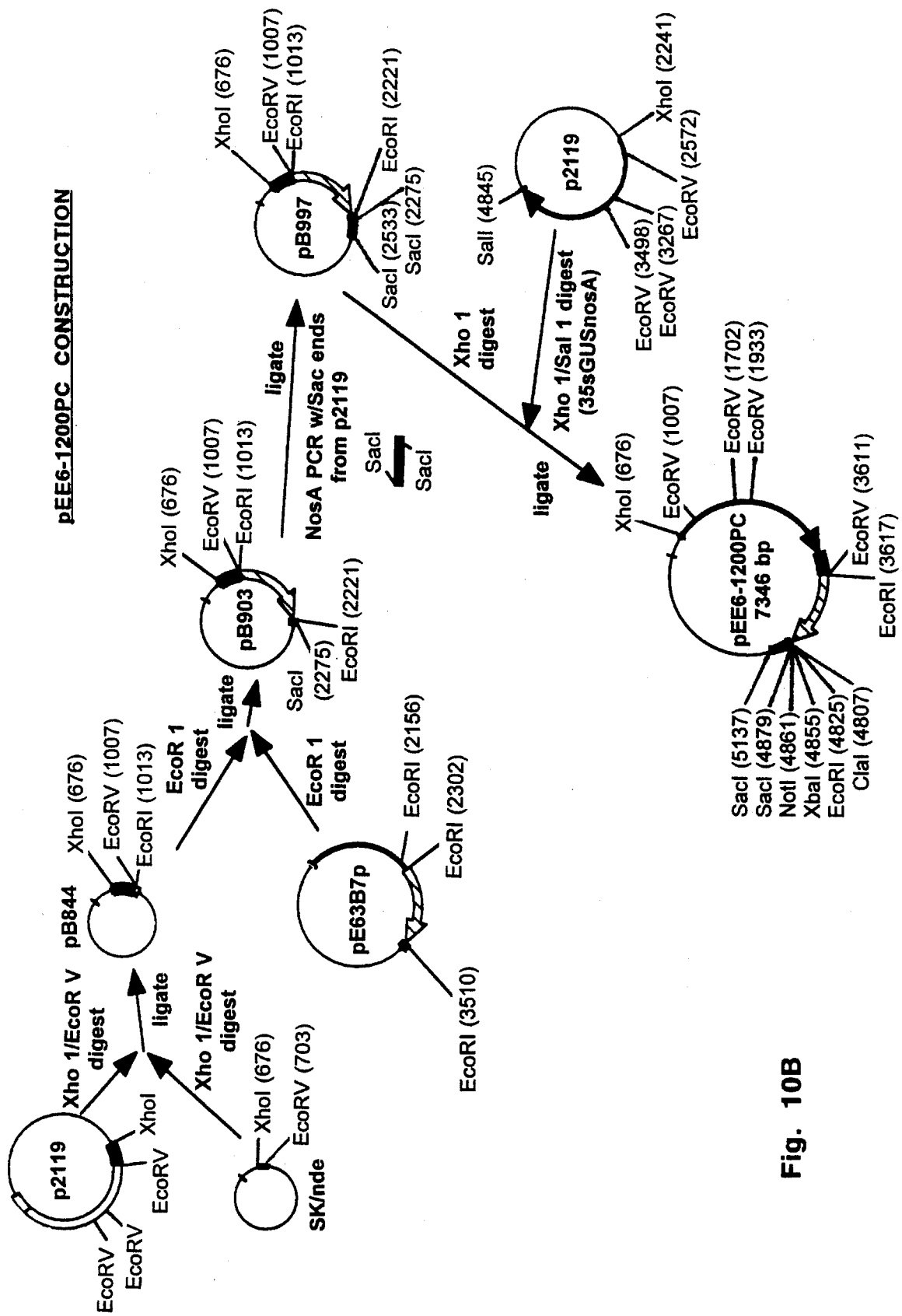

A polyadenylation region from the nopaline synthase (Nos) gene of Agrobacterium Ti plasmid was PCR amplified with primers containing Sac-1 sites from p2119 and cloned into the Sac 1 site of pB903 to generate pB997. A marker gene beta-glucuronidase (GUS) was added to this plasmid as follows: pB997 was linearized at Xho 1 and the 35S-GUS/ Nos A (Xho 1/Sal 1) fragment from p2119 was added to generate pEE6-1200PC, shown in FIG. 10A. pEE6-1200PC has unique Cla-1, Xba-1, and Not-1 sites. The construction of pEE6-1200PC is shown in FIG. 10B.

The following peroxidase genes were cloned and incorporated into pEE6-1200PC or other expression vectors.

2. TPA-1 Tobacco Peroxidase

Figure 11:
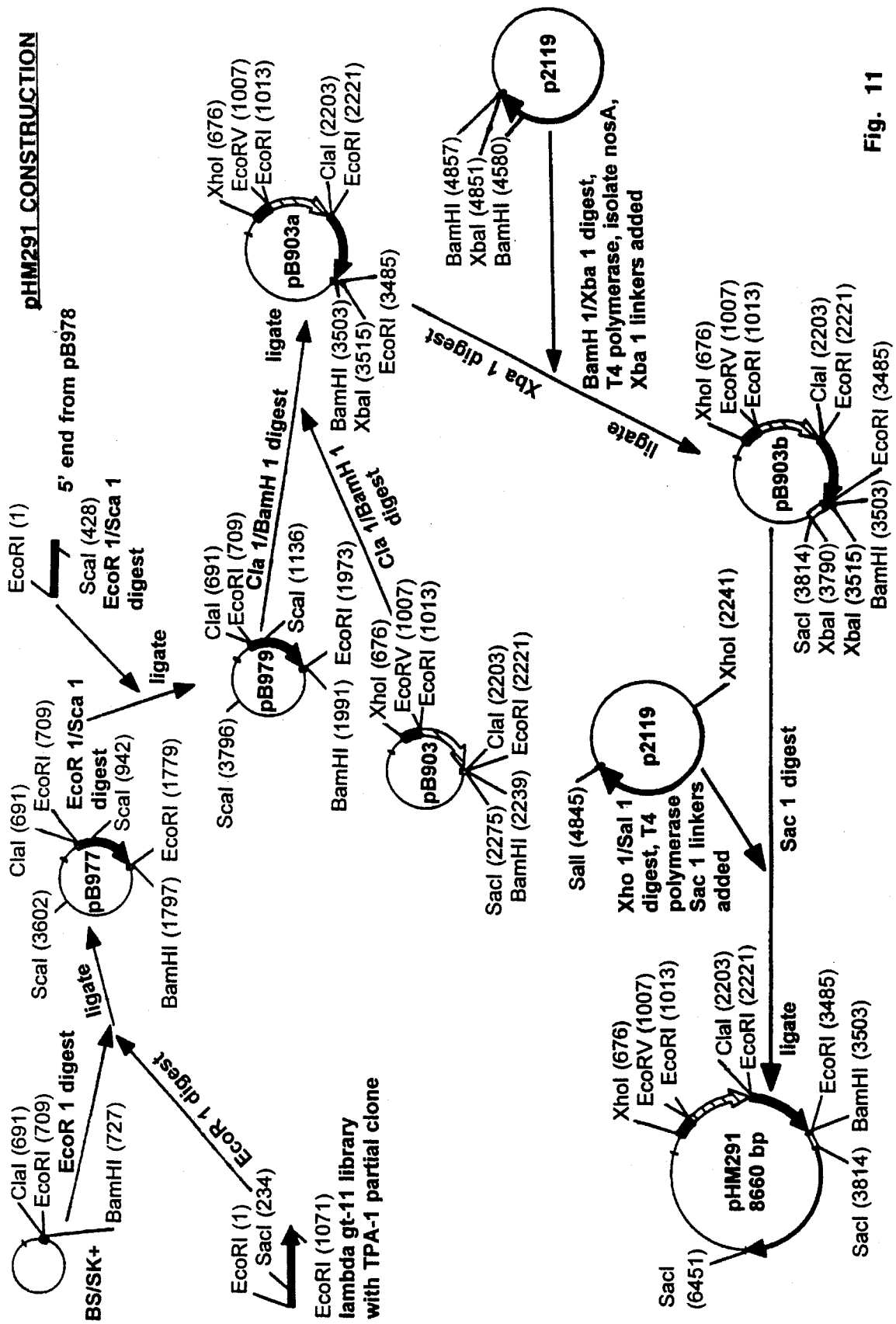
FIG. 11 describes the construction of HM291.
Figure 12:
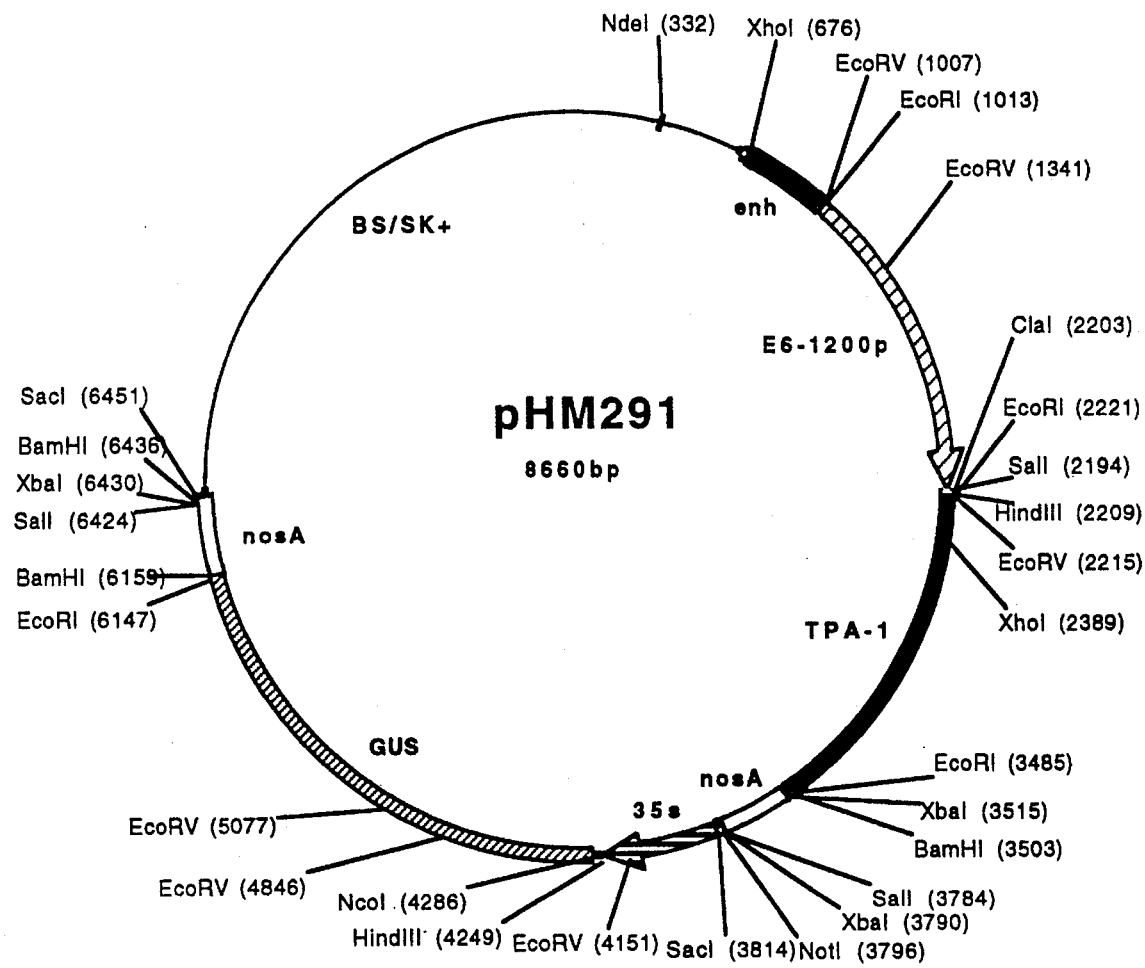
FIG. 12 is the restriction map of HM291.

TPA-1 (Lagrimini, *Proc. Natl. Acad. Sci.* 84:7542–7546, 1987) is a 32 kDa, anionic (pI, 4.45) tobacco peroxidase. Two isozymes, encoded by a pair of alleles, give a total of four anionic peroxidase genes in *Nicotiana tabacum*. The RNA is primarily found in stem tissue, but also at lower levels in leaf and root. FIGS. 11 and 12 describe the construction and restriction map of pHM291, an expression vector containing the TPA-1 cDNA.

A DNA probe for TPA-1 was cloned through polymerase chain reaction using primers 3 and 4 (SEQ ID NOs:24 and 25). The probe was hybridized to *Nicotiana tabacum* 30-day seedling cDNA library (obtained from Clontech) from which a 1065 bp cDNA fragment was isolated and subcloned into BS/SK+ at the EcoR-1 site to generate pB977. Sequence analysis showed that this cDNA was missing approximately 200 bases from the 5' end. Two additional primers, 5 (containing an EcoR 1 site) and 6, were synthesized and the remaining 5' end along with an additional 250bp was amplified through RT/PCR, subcloned into pT7Blue (Novagen) to generate pB978. (Primers 5 and 6 are described below at SEQ ID NOs: 26 and 27.) The clone showed complete homology to the published sequence. The 1065 bp and 425 bp fragments were digested with Eco-R1/Sca-I, religated, and cloned into BS/SK+ vectors. The clone containing the correct fragment (1250bp) was identified by restriction mapping to generate pB979.

Plasmid B979 was then digested with Cla-1/Bam-1 and ligated into pB903 to generate pB903a. The 277 bp poly(A) signal, NosA, was isolated from p2119 by digestion with BamH-1/Xba-1.

The fragment was treated with T4 DNA polymerase. Xba-1 linkers were added, and the fragment was ligated into pB903a at the Xba-1 site to generate pB903b. The marker gene 35S-GUS was then isolated from p2119 (Xho-1/Sal-1), blunt ended, and cloned into pB903b at the Sac-1 site after addition of Sac-I linkers to generate pHM291.

3. ARP Arabidopsis Peroxidase

ARP (Intapruk, *Ferment. Bio. Eng.* 75:166–172, 1993) is a 36 kDa, cationic (pI, 8.89) Arabidopsis peroxidase. A horseradish peroxidase gene (Fujiyama, *Eur. J. Biochem.* 173:681–687, 1988) (see section 4, below) was used to probe a 4.5 week leaf/stem *Arabidopsis thaliana* cDNA library (Clontech). A clone of approximately 1125 bp that hybridized to HRPC was isolated. About 100 bases were sequenced from both 5' and 3' ends and showed complete homology to a published sequence of ARP (prxCb) (Intapruk, *Plant Physiol.* 104:285–286, 1994). The ARP clone we isolated is a full-length cDNA clone.

Figure 13:
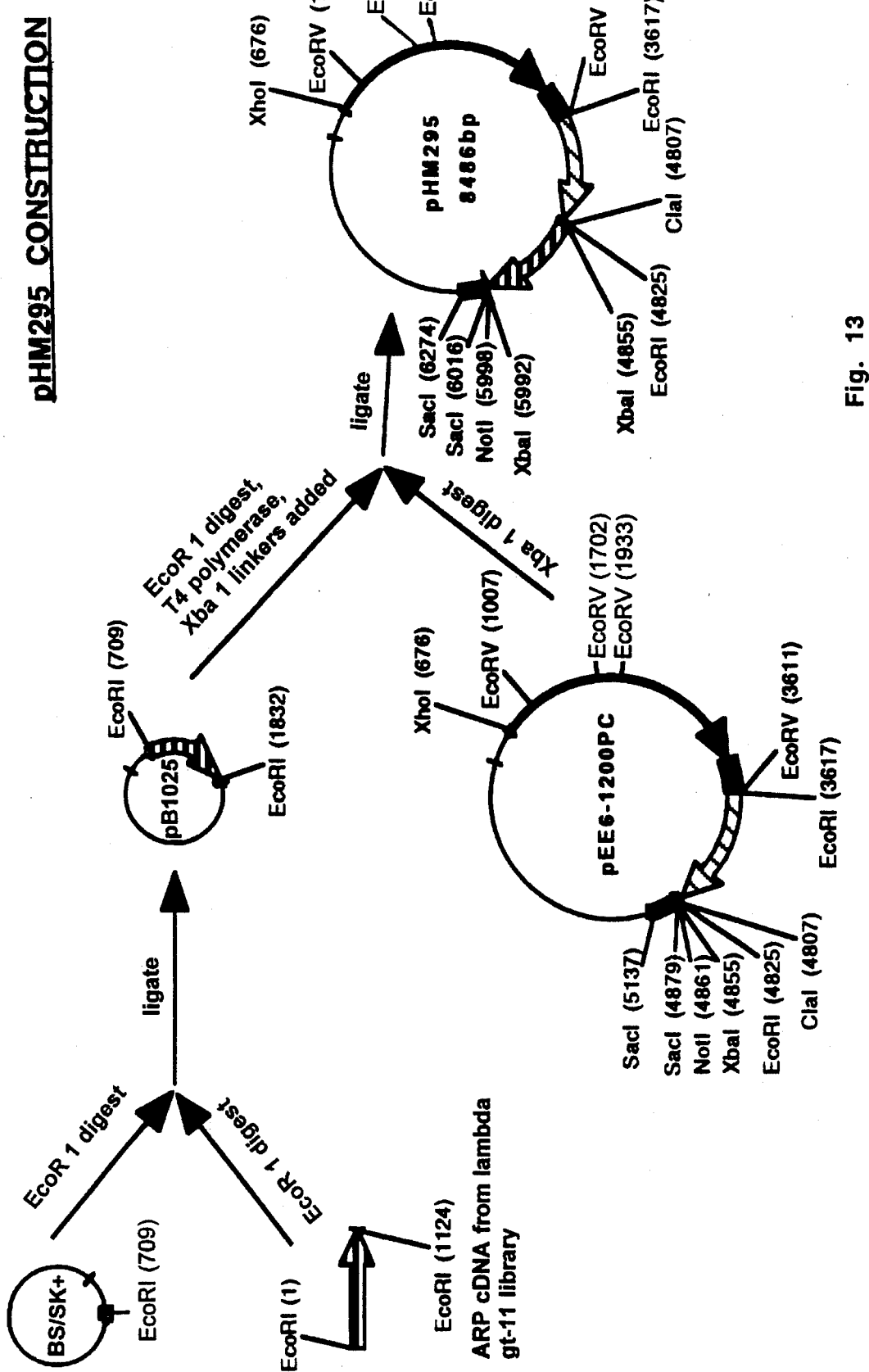
FIG. 13 describes the construction of HM295.
Figure 14:
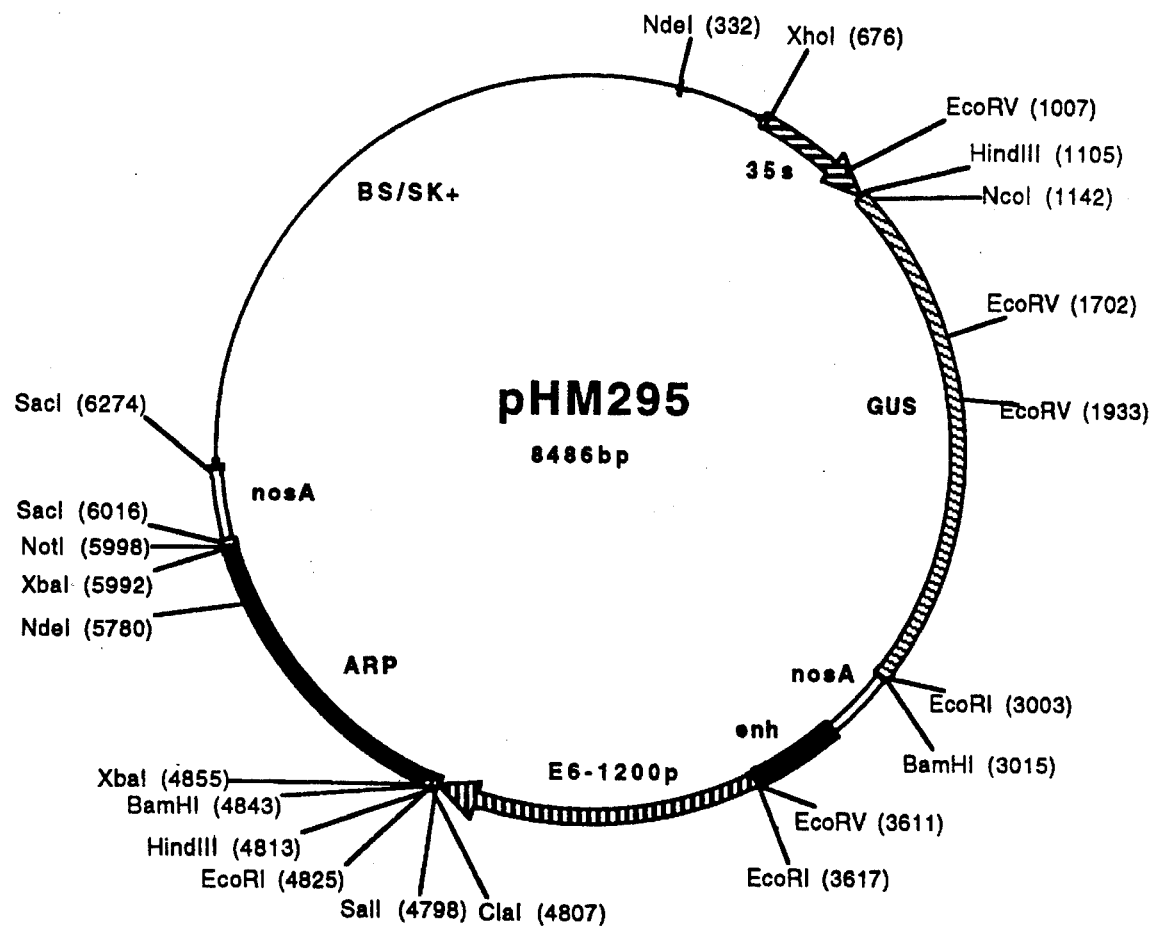
FIG. 14 is the restriction map of HM295.

The fragment was subcloned into Bluescript/SK+ at the EcoR-1 site to generate pB1025. Xba-1 linkers were added to this fragment and it was then cloned into the pEE6-1200PC vector at Xba-1 site to generate pHM295. FIGS. 13 and 14 describe the construction and restriction map of HM295.

4. Horseradish Peroxidase

Figure 15:
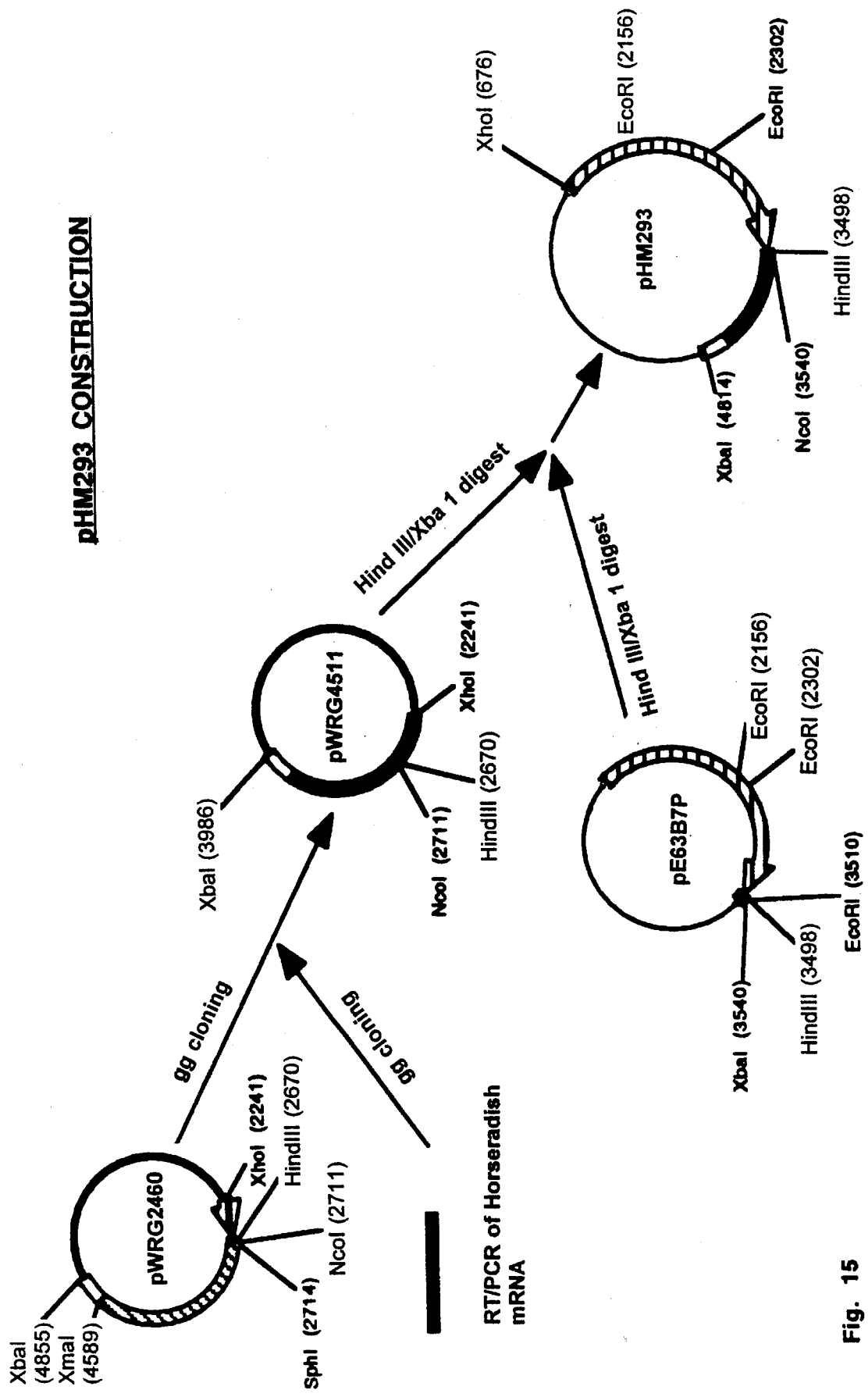
FIG. 15 describes the construction of HM293.

HRPC (prxCl) (Fujiyama, *Eur. J. Biochem.* 173:681–687, 1988) is a 34 kDa, moderately anionic (pI, 5.77) peroxidase. There are more than 30 iso-forms of HRPCs. The prxCl gene was amplified through RT/PCR using primers 7 and 8 (SEQ ID NOs: 28 and 29) and horseradish root mRNA and then cloned into a plant expression vector, pWRG2460, by "GG cloning" to give plasmid pWRG4511. The plasmid WRG2460 is a modified p2119. A restriction map of pWRG2460 is shown in FIG. 15. The PRC product was sequenced and was in agreement with the published sequence of prxCl.

The GG-cloning method is a simple method of cloning PCR generated fragments. The method relies on the unique Xma-1 and Sph-1 site in the vector accepting the fragment with two guanosine residues on the 5' ends. The vector was digested with Xma-I/Sph-1, phenol/chloroform extracted, and precipitated. The vector is then blunt-ended with Klenow enzyme, using only dCTP (which left the vector with a 3' CC overhang), phenol/chloroform extracted, and precipitated. The PCR product (with GG 5' ends) was loaded onto a Centricon 100 (Amicon) and spun to get rid of the nucleotides/primers. The PCR product was then incubated with T4 DNA polymerase in a mix lacking dCTP, which left a 5' GG overhang. It was then phenol/chloroform-extracted and precipitated.

Figure 16:
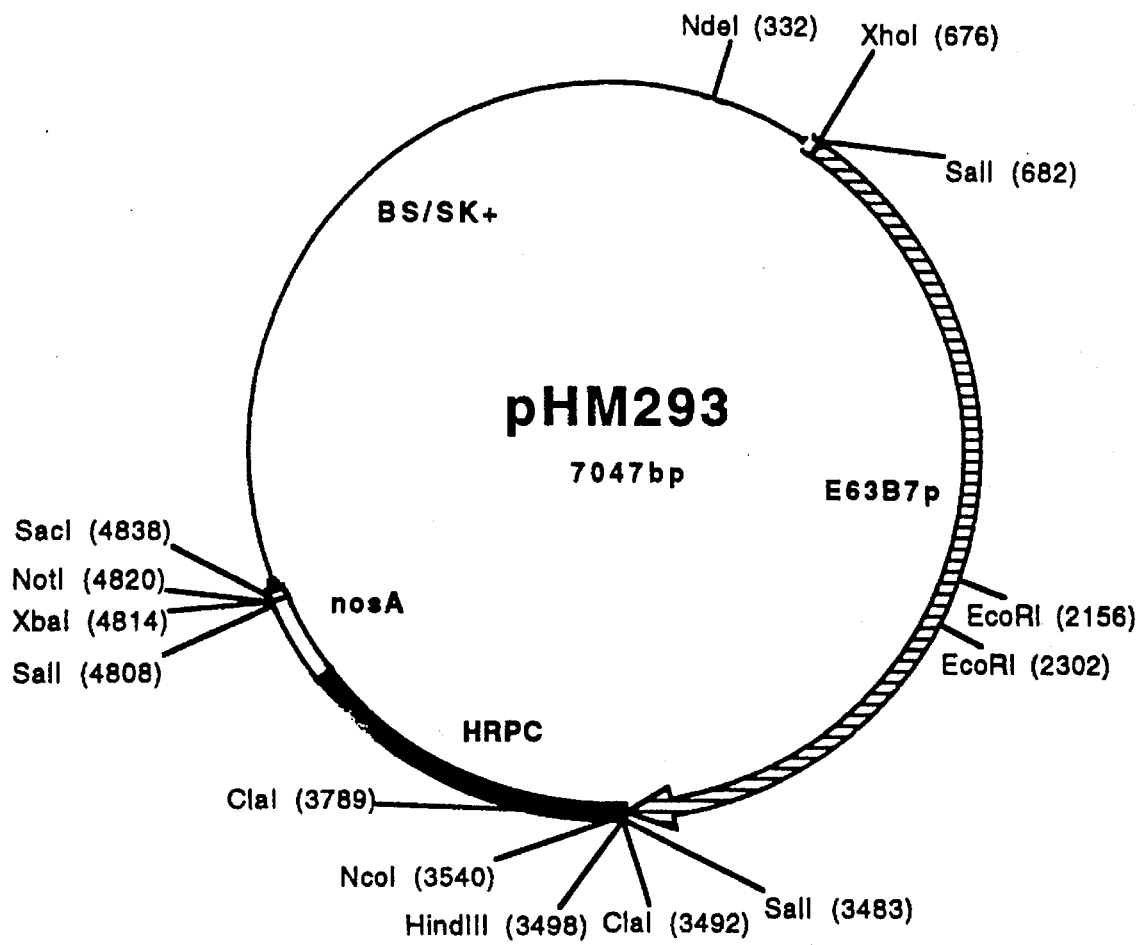
FIG. 16 is the restriction map of HM293.

The digested vector pWRG2460 and the PCR product were then ligated together to generate pWRG4511. pWRG4511 was digested with Hind-3/Xba-1, and the prxC1 fragment along with an AMV leader and NosA were ligated into plasmid pE6-3B7P to generate pHM293. FIG. 15 describes the construction of HM293, an expression vector containing prxC1. FIG. 16 describes the restriction map of pHM293.

5. Results

The gene constructs were then introduced into DP50 cotton through particle bombardment, as described above. Transgenic cotton plants were screened for fiber strength. The results for each peroxidase construct are given below in Tables 9, 10 and 11.

Tobacco peroxidase (TPA-I) increased the fiber strength up to 23% above DP 50 control plants (Table 9).

Horseradish peroxidase gene increased the fiber strength up to 54% over DP50 control plants (Table 10).

Arabidopsis peroxidase gene (ARP) increased the fiber strength by 31% over DP50 control plants (Table 11).

TABLE 9

Transgenic Cotton Containing Tobacco Peroxidase Gene (TPA-I)

| Plant | Strength g/tex | Length inches | Micronaire | % Strength Increase |
|---|---|---|---|---|
| #6334 | 23.2 | 1.22 | 4.4 | 23.4 |
| #6844 | 22.9 | 1.23 | 4.8 | 21.8 |
| #6843 | 22.7 | 1.24 | 3.3 | 20.7 |
| #6322 | 22.5 | 1.14 | 3.9 | 19.7 |
| #6842 | 22.5 | 1.21 | 3.9 | 19.7 |
| #6723 | 22.2 | 1.30 | 3.0 | 18.1 |
| #6983 | 22.0 | 1.20 | 4.8 | 17.0 |
| #6965 | 22.0 | 1.17 | 3.2 | 17.0 |
| #6396 | 21.6 | 1.23 | 4.1 | 14.9 |
| #6249 | 21.3 | 1.19 | 3.5 | 13.3 |
| #6296 | 21.1 | 1.27 | 4.0 | 12.2 |
| #6846 | 20.9 | 1.12 | 3.7 | 11.2 |
| DP50 Control | 18.8 ± 0.7 | 1.17 ± 0.04 | 3.9 ± 0.4 | |

Notes:
Total of 52 plants analyzed.
Stelometer data.
Remaining plants show normal fiber properties.

TABLE 10

Transgenic Cotton Containing Horseradish Peroxidase Gene

| Plant | Strength g/tex | Length inches | Micronaire | % Strength Increase |
|---|---|---|---|---|
| #7083 | 28.9 | 1.16 | 2.8 | 53.7 |
| #7120 | 23.9 | 1.01 | 3.6 | 27.1 |
| #7477 | 23.8 | 1.14 | 4.8 | 26.6 |
| #6979 | 22.3 | 1.00 | 4.6 | 18.6 |
| #7080 | 22.3 | 1.02 | 3.6 | 18.6 |
| #7398 | 22.3 | 1.13 | 3.8 | 18.6 |
| #7030 | 22.1 | 1.20 | 3.6 | 17.6 |
| #7081 | 22.1 | 1.19 | 3.7 | 17.6 |
| #7112 | 22.1 | 1.18 | 3.1 | 17.6 |
| #7401 | 21.9 | 1.19 | 2.6 | 16.5 |
| #7152 | 21.7 | 1.22 | 4.5 | 15.4 |
| #7122 | 21.5 | 1.20 | 2.9 | 14.4 |
| #7046 | 21.4 | 1.12 | 4.2 | 13.8 |
| #7159 | 21.1 | 1.10 | 3.6 | 12.2 |
| #6992 | 21.1 | 1.23 | 3.1 | 12.2 |
| #7097 | 20.9 | 1.10 | 3.9 | 11.2 |
| #7160 | 20.9 | 1.24 | 3.7 | 11.2 |
| DP50 Control | 18.8 ± 0.7 | 1.17 ± 0.04 | 3.9 ± 0.4 | |

Notes:
Total of 44 plants analyzed.
Stelometer data.
Remaining plants show normal fiber properties.

TABLE 11

Transgenic Cotton Containing Arabidopsis Peroxidase Gene

| Plant | Strength g/tex | Length inches | Micronaire | % Strength Increase |
|---|---|---|---|---|
| #7712 | 24.6 | 1.25 | 4.3 | 30.9 |
| #7592 | 22.8 | 1.18 | 4.5 | 21.3 |
| #7980 | 21.7 | 1.20 | 2.9 | 15.4 |
| #7596 | 21.5 | 1.19 | 4.6 | 14.4 |
| DP50 Control | 18.8 ± 0.7 | 1.17 ± 0.04 | 3.9 ± 0.4 | |

Notes:
Total of 12 plants analyzed.
Stelometer data.
Remaining plants show normal fiber properties.

I claim:

1. A cotton plant comprising in its genome a heterologous genetic construct comprising (a) a seed floss fiber-specific promoter isolated from cotton plants; and (b) a coding sequence encoding a peroxidase, wherein the promoter is operably linked to the coding sequence, wherein the peroxidase is expressed in the plant seed floss fiber and wherein the coding sequence and promoter are not natively together and wherein the seed floss fiber has an increase in fiber strength as compared to a non-transformed control plant seed floss fiber.

2. The plant of claim 1 wherein the peroxidase is expressed as RNA at a level equal to or greater than 5-fold the native peroxidase expression level.

3. The plant claim 1, wherein the construct additionally contains a marker sequence.

4. The plant of claim 3 wherein the marker sequence is for the GUS gene.

5. The plant of claim 1, wherein the sequence of the fiber-specific promoter is substantially similar to SEQ ID NO: 4.

6. The plant of claim 1, wherein the sequence of the fiber-specific promoter is substantially similar to SEQ ID NO: 5.

7. The plant of claim 1, wherein the plant is DP-50 cotton.

8. Seeds of the plant of claim 1 which contain the heterologous construct.

9. A cotton plant comprising in its genome a heterologous genetic construct comprising (a) a seed floss fiber-specific promoter isolated from cotton plants, wherein the promoter is selected from the group of E6-3B and B8 promoters; and (b) a coding sequence encoding a peroxidase, wherein the promoter is operably linked to the coding sequence, wherein the peroxidase is expressed in the plant seed floss fiber and wherein the seed floss fiber has increased strength.

* * * * *

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
( A ) LENGTH: 26 base pairs
( B ) TYPE: nucleic acid (C) STRANDEDNESS: single
(D) TOPOLOGY: linear (ii) MOLECULE TYPE: oligonucleotide (iii) HYPOTHETICAL: YES (xi) SEQUENCE DESCRIPTION: SEQ ID NO:1:

ATGCTGGTAC CTTTTTTTTT TTTTTT    26

(2) INFORMATION FOR SEQ ID NO:2:

(i) SEQUENCE CHARACTERISTICS:
(A) LENGTH: 1067 base pairs
(B) TYPE: nucleic acid
(C) STRANDEDNESS: double
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: Gossypium hirsutum
(B) STRAIN: Coker 312
(D) DEVELOPMENTAL STAGE: 15 day old fiber cells
(F) TISSUE TYPE: fiber cells (vii) IMMEDIATE SOURCE:
(A) LIBRARY: CKFB15A1
(B) CLONE: E6

(xi) SEQUENCE DESCRIPTION: SEQ ID NO:2:

ACACACACAA GTAAAGCATT AGCAACCATA GCCATGGCTT CCTCACCAAA ACTCTTCTCT    60
ATGTCTATCC TCTTCCTTTT TGCCCTCTTC TCCATGCAAA TCCATGCTAG AGAGTACTTC    120
AGCAAATTCC CAAGAGTTAA CATCAATGAG AAAGAGACAA CAACCAGAGA GCAAAAGCAC    180
GAGACCTTCG TTCCCCAGAC CACCCAAAAG CCAGAAGAAC AAGAGCCAAG GTTCATTCCT    240
GAAACCCAAA ATGGTTATGG CCTTTACGGC CACGAGTCAG GCTCAAGCCG GCCCAGTTTC    300
ACCACCAAAG AAACCTATGA ACCCTATGTC ACCCCTGTTA GATTCCACCC TGATGAGCCC    360
TATAACAGCA TCCCCGAATC CTCCAACAAT AAAGACACTT ACTACTACAA CAAGAATGCC    420
TACGAGTCCA CTAAGCAGCA AAACTTGGGC GAGGCCATTT TCACCGAGAA AGGATGGAGC    480
ACCAAGGAAA ACCAGAACAA CAACTACTAC AACGGCAACA ATGGTTACAA CAATGGCGAG    540
AAGCAAGGCA TGAGCGATAC TAGGTACTTG GAGAATGGAA AGTACTACTA TGACGTCAAG    600
AGTGAGAACA ACTATTATCC AAACCGGTTC GACAACTCAA GAGGAGTTGC TTCGAGGAAC    660
GAGTTCAATG AGAATCGTTA CAACAACATG GGAAGGTACC ACCAGAACCA AGAGGAGTTC    720
GAGGAAAGCG AGGAAGAGTT CGAACCCTGA TCACCTGTCG TACAGTATTT CTACATTTGA    780
TGTGTGATTT GTGAAGAACA TCAAACAAAA CAAGCACTGG CTTTAATATG ATGATAAGTA    840
TTATGGTAAT TAATTAATTG GCAAAAACAA CAATGAAGCT AAAATTTTAT TTATTGAGCC    900
TTGCGGTTAA TTTCTTGTGA TGATCTTTTT TTTTATTTTC TAATTATATA TAGTTTCCTT    960
TGCTTTGAAA TGCTAAAGGT TTGAGAGAGT TATGTTCTTT TTCTCTTCCT CTTTCTTTTT    1020
TAACTTTATC AAACAATTTT TGAATAAAAA TGTGAGTATA TTGTAAC    1067

(2) INFORMATION FOR SEQ ID NO:3:

(i) SEQUENCE CHARACTERISTICS:
(A) LENGTH: 690 base pairs
(B) TYPE: nucleic acid (C) STRANDEDNESS: double
(D) TOPOLOGY: linear (i i) MOLECULE TYPE: cDNA (i i i) HYPOTHETICAL: NO (i v) ANTI-SENSE: NO (v i) ORIGINAL SOURCE:
(A) ORGANISM: Gossypium hirsutum
(B) STRAIN: Coker 312
(D) DEVELOPMENTAL STAGE: 15 day old fiber cells
(F) TISSUE TYPE: fiber cells (v i i) IMMEDIATE SOURCE:
(A) LIBRARY: CKFB15A1
(B) CLONE: B8

(x i) SEQUENCE DESCRIPTION: SEQ ID NO:3:

| | | | | | | |
|---|---|---|---|---|---|---|
| CACCAACGGA | CAATGCTTTC | TCCAGCCTTA | AATCGGGCAC | ATTGAATTCA | CTCACCGATG | 60 |
| AACAAAAAGT | GGAGCTGGTG | CAATTCCACA | TCGTCCCAAC | ATACCTCACC | TCGTCTCAGT | 120 |
| TCCAAACCAT | TAGCAATCCT | TTGAGAACCC | AAGCTGGTGA | TAGTGGCGAT | GGCAAGTTCC | 180 |
| CTCTCAATAT | CACCACTTCG | GGGAACTCCG | TGAATATAAC | AACAGGGTTG | ACAAACACCA | 240 |
| GTGTTTCCGG | CACTATTTAC | ACTGATGGTC | AGCTTGCTGT | TTATCAAATC | GATCAAGTTC | 300 |
| TTCAACCATT | GCAAATATTT | GCACCTAGGC | CTCCAGCTCC | AGCACCGGCA | CCGGCAAAGT | 360 |
| CGAAGAATAA | GAAGGCTACC | ACCGTTGCTG | ATAGCCCCGA | TGTTACCCCA | GCTGATAACT | 420 |
| CCAAAGCGGC | CACCTTGCAA | AATGTTGGTT | TGTTTGGAGT | TGCTGCTCTA | GTTATTGCAC | 480 |
| TTTCTTTGTG | ACCATGAAAA | TGGAGAAAAG | AAGAAGACAG | TGATTTTGAT | GGTGATCAAG | 540 |
| ATGGCGAGTG | TTTTTTATTT | TTTCAATAAT | TATCATTTAA | AAAATTTATG | TTCTGTATGA | 600 |
| ANGATTGAAT | TTTGAGTTTG | TCTTGTTGAT | TTCATTTATT | TTTGTTTTGA | AATTTTCTTT | 660 |
| GTTATCTCTT | ATTTCTCAAT | TGTAATTGTG | | | | 690 |

(2) INFORMATION FOR SEQ ID NO:4:

(i) SEQUENCE CHARACTERISTICS:
(A) LENGTH: 614 base pairs
(B) TYPE: nucleic acid
(C) STRANDEDNESS: double
(D) TOPOLOGY: linear (i i) MOLECULE TYPE: DNA (genomic)

(i i i) HYPOTHETICAL: NO (i v) ANTI-SENSE: NO (v i) ORIGINAL SOURCE:
(A) ORGANISM: Gossypium barbadense
(B) STRAIN: Sea Island (v i i) IMMEDIATE SOURCE:
(A) LIBRARY: EMBL-SI
(B) CLONE: E6-3B (x i) SEQUENCE DESCRIPTION: SEQ ID NO:4:

| | | | | | | |
|---|---|---|---|---|---|---|
| AAATTATAGC | ATACCTCACG | ATGTGGGTGA | AGTAAAATTA | TTTAACAAAT | ATATTTGAA | 60 |
| AAATTGATAA | AAATACTAAA | TGAGGTTTTG | GTTGAATAGT | AAGATATAAT | TATTACAAAT | 120 |
| TATAAATATG | TAGGTTCAAA | ATCTATCATG | TGTATATTTG | TACTATTATT | CTATATAAAT | 180 |
| TGATAACCTT | ATAAAAGTAT | CTAATTTAGT | TTATGGTTGA | TTGATCGATA | ATACCAAATT | 240 |
| TATTAAAAAT | TAATATTAGT | AAAGATATAT | AGTACAAAAC | TAAACATAAA | ATTTTATATG | 300 |

| | | | | | | |
|---|---|---|---|---|---|---|
| TTAAGGAAAT | AGCGGAAAAA | ATATCATATT | TGTAGAACTG | TTTAGCAGTG | TGGGAGAATG | 360 |
| GGATCATTAC | AAGGAAAAAT | GAAATATATA | TCATTAATAC | CAAACATAAA | AGAAAGCGTC | 420 |
| TTTTGATAAA | GTTGTTATTG | GTGTAATGTG | AAGGGACCAC | AATCATCACC | ATTCACCACT | 480 |
| TGCTCCTAAT | TGAGTTGAAA | TCTTTTTACA | ACATAGAAAA | CTAGAAGATC | GCCCTTTCTT | 540 |
| GCTTCATATA | TATAGATTTT | GTATCATCGC | AATTTCACAT | CACACACACA | AGTAAAGCAT | 600 |
| TAGCAACCAT | AGCC | | | | | 614 |

( 2 ) INFORMATION FOR SEQ ID NO:5:

( i ) SEQUENCE CHARACTERISTICS:
        ( A ) LENGTH: 307 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Gossypium barbadense
        ( B ) STRAIN: Sea Island ( v i i ) IMMEDIATE SOURCE:
        ( A ) LIBRARY: EMBL-SI
        ( B ) CLONE: SIB8

( x i ) SEQUENCE DESCRIPTION: SEQ ID NO:5:

| | | | | | | |
|---|---|---|---|---|---|---|
| TTTTTAATGG | TGTTGGATGG | TTATATTATA | TCTCGATTAT | ATATATTTTT | TTTAAAAACC | 60 |
| GAAGTTGAAT | GTCTAAATAG | GAAGTAATTT | TTTTAATATT | ATTTTTTTAT | AATATTTGAA | 120 |
| TCCGATATCT | TATTTAAAAA | CCATCGAAAT | TTTTATTACT | CAATCATTAC | CGAAATAGAA | 180 |
| TCGGGCTAAA | ATATTTCGAA | AACTAAAGT | TTCACTTTTT | ATATTGAAAA | ACGAGGCTTT | 240 |
| GTGATTCTTA | TAAATTTAAT | TCATTGAAAT | TTCATCAAGT | AAAACAGAAG | AATTATAAAT | 300 |
| CTCTAAA | | | | | | 307 |

( 2 ) INFORMATION FOR SEQ ID NO:6:

( i ) SEQUENCE CHARACTERISTICS:
        ( A ) LENGTH: 313 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

| | | | | | | |
|---|---|---|---|---|---|---|
| TCACCTGTCG | TACAGTATTT | CTACATTTGA | TGTGTGATTT | GTGAAGAACA | TCAAACAAAA | 60 |
| CAAGCACTGG | CTTTAATATG | ATGATAAGTA | TTATGGTAAT | TAATTAATTG | GCAAAAACAA | 120 |
| CAATGAAGCT | AAAATTTTAT | TTATTGAGCC | TTGCGGTTAA | TTTCTTGTGA | TGATCTTTTT | 180 |
| TTTTATTTTC | TAATTATATA | TAGTTTCCTT | TGCTTTGAAA | TGCTAAAGGT | TTGAGAGAGT | 240 |
| TATTGCTCTT | TTTTTCTTCC | TCTTTCTTTT | TTAACTTTAT | CATACAAATT | TTGAATAAAA | 300 |
| ATGTGAGTAC | ATT | | | | | 313 |

( 2 ) INFORMATION FOR SEQ ID NO:7:

( i ) SEQUENCE CHARACTERISTICS:
 ( A ) LENGTH: 18 base pairs
 ( B ) TYPE: nucleic acid
 ( C ) STRANDEDNESS: single
 ( D ) TOPOLOGY: linear ( i i ) MOLECULE TYPE: oligonucleotide ( i i i ) HYPOTHETICAL: YES ( i v ) ANTI-SENSE: NO ( x i ) SEQUENCE DESCRIPTION: SEQ ID NO:7:

ACCGAAATAG AATCGGGC 18

( 2 ) INFORMATION FOR SEQ ID NO:8:

( i ) SEQUENCE CHARACTERISTICS:
 ( A ) LENGTH: 31 base pairs
 ( B ) TYPE: nucleic acid
 ( C ) STRANDEDNESS: single
 ( D ) TOPOLOGY: linear ( i i ) MOLECULE TYPE: oligonucleotide ( i i i ) HYPOTHETICAL: YES ( x i ) SEQUENCE DESCRIPTION: SEQ ID NO:8:

GGAATTCGGA TCCTTTAGAG ATTTATAATT C 31

( 2 ) INFORMATION FOR SEQ ID NO:9:

( i ) SEQUENCE CHARACTERISTICS:
 ( A ) LENGTH: 29 base pairs
 ( B ) TYPE: nucleic acid
 ( C ) STRANDEDNESS: single
 ( D ) TOPOLOGY: linear ( i i ) MOLECULE TYPE: oligonucleotide ( i i i ) HYPOTHETICAL: YES ( x i ) SEQUENCE DESCRIPTION: SEQ ID NO:9:

CCGTTAAGCT TTGATCACCT GTCGTACAG 29

( 2 ) INFORMATION FOR SEQ ID NO:10:

( i ) SEQUENCE CHARACTERISTICS:
 ( A ) LENGTH: 29 base pairs
 ( B ) TYPE: nucleic acid
 ( C ) STRANDEDNESS: single
 ( D ) TOPOLOGY: linear ( i i ) MOLECULE TYPE: oligonucleotide ( i i i ) HYPOTHETICAL: YES ( x i ) SEQUENCE DESCRIPTION: SEQ ID NO:10:

TGACAGGATC CGTTACAATA TACTCACAT 29

( 2 ) INFORMATION FOR SEQ ID NO:11:

( i ) SEQUENCE CHARACTERISTICS:
 ( A ) LENGTH: 29 base pairs
 ( B ) TYPE: nucleic acid
 ( C ) STRANDEDNESS: single
 ( D ) TOPOLOGY: linear ( i i ) MOLECULE TYPE: oligonucleotide ( i i i ) HYPOTHETICAL: YES ( x i ) SEQUENCE DESCRIPTION: SEQ ID NO:11:

GGAATCTGCA GTGATCACCT GTCGTACAG                                29

( 2 ) INFORMATION FOR SEQ ID NO:12:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: oligonucleotide ( i i i ) HYPOTHETICAL: YES ( x i ) SEQUENCE DESCRIPTION: SEQ ID NO:12:

TTGCTCGAGT CGACGGATCT AGTAACATAG                               30

( 2 ) INFORMATION FOR SEQ ID NO:13:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:13:

GGCCAGGATC CATGTCTTTT TTAAGA                                   26

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:14:

TGCACCTGAT AGAGCAAC                                            18

( 2 ) INFORMATION FOR SEQ ID NO:15:

( i ) SEQUENCE CHARACTERISTICS:
        ( A ) LENGTH: 1064 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:15:

GAATTCCGGA ATCATGGAAA TGATGGATCA ATTTTGTTAG ACACAGATGG GATACAAACT    60
GAGAAAGATG CAATTCCTAA TGTAGGTGCA GGAGGATTTG ATATTGTTGA TGATATTAAA   120
ACTGCATTAG AGAATGTATG CCCTGGTGTT GTATCATGTG CAGATATTTT AGCCCTTGCA   180
TCTGAAATTG GAGTTGCCTT GGCTGGAGGT CCATGCTGGC AAGTACTTTT TGGCAGAAGA   240
GATAGCTTAA CAGCAAACCG ATCTGGAGCT AATAGTGATA TTCCTAGCCC CTTTGAAACC   300
CTTGCTGTAA TGACGCCACA ATTCACCAAC AAGGGAATGG ATTTAACTGA TCTTGTTGCT   360
CTATCTGGTG CACACACATT TGGAAGAGCA AGATGTGGTA CTTTTGAACA ACGTCTCTTT   420
AACTTCAGTG GCAGTGGTAA TCCTGATCCA ACCGTAGACG CTACATTTTT ACAAACATTA   480

```
CAGGGAATTT GTCCTCAAGG TGGAAATAAT GGCAATACTT TTACAAATCT TGATATATCA    540

ACTCCTAATG ATTTTGATAA TGACTATTTC ACTAATCTTC AAAATAATCA AGGACTTCTT    600

CAAACTGATC AAGAGTTGTT TTCTACATCT GGATCTGCTA CAATTGCTAT AGTGAATCGT    660

TATGCTGGTA GTCAAAGTCA GTTTTTTGAT GATTTATTT GCTCGATGAT TAAATTGGGT     720

AATATAAGTC CATTAACTGG TACTAATGGA GAGATTAGGA AAGATTGCAA GAGGGTTAAT    780

TAATTAATTA ATTAATTAAT CAAGCAGATT ATATTAATTA TCAAGATCGA GTGCTTTAAT    840

TTCTGCATGT TCTTGTGTTG TTTAATCATG TCCTAAAGAA AGATTGTCAG AAGTTTGATG    900

TCATGAGTTG TAAATTTTTT TCATCTTTTT GACGCTTATT TTGTTTATG TAAATGTAAT     960

ATGTGCTGAA ATGGCAATTC CAATAAGGAT GTTATGCTGA AATAGCAATT CCAATAATTA   1020

AGGATTTAAT CCAAAAAAAA AAAAAAAAA AAAAACCGGA ATTC                     1064
```

( 2 ) INFORMATION FOR SEQ ID NO:16:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:16:

```
TCGTCCACTG CCCAATCTTA GAG                                              23
```

( 2 ) INFORMATION FOR SEQ ID NO:17:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:17:

```
CGTTGCCTTT GATCCATAAC ACC                                              23
```

( 2 ) INFORMATION FOR SEQ ID NO:18:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:18:

```
AGACACAGAT GGGACTCAAA CTGAG                                            25
```

( 2 ) INFORMATION FOR SEQ ID NO:19:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:19:

```
CAACTCCAAT TTCAGATGCA AGGG                                             24
```

( 2 ) INFORMATION FOR SEQ ID NO:20:

( i ) SEQUENCE CHARACTERISTICS:
        ( A ) LENGTH: 681 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:20:

| | | | | | | |
|---|---|---|---|---|---|---|
| GAATTCCGGG | ATGATATTAA | AACTGCACTA | GAGAATGTAT | GCCCTGGTGT | TGTATCTTGT | 60 |
| GCAGATATTT | TAGCCCTTGC | ATCTGAAATT | GGAGTTGTCT | TGGCTAAAGG | TCCGTCGTGG | 120 |
| CAAGTACTTT | TTGGCAGAAA | AGACAGCTTA | ACAGCAAACC | GATCTGGAGC | TAATAGTGAT | 180 |
| ATTCCTAGCC | CCTTTGAAAC | ACTTACGGTG | GATACCTAGG | CACCCAGAGA | CGAGGAAGGG | 240 |
| CGTAGTAATC | GACGAAATGC | TTCGGGGAGT | TGAAAATAAG | CATAGATCCG | GAGATTCCCG | 300 |
| AATAGGCAAC | CTTTCGAACT | GCTGCTGAAT | CCATGGGCAG | GCAAGAGCAA | CCTGGCGAAC | 360 |
| TGAAACATCT | TAGTAGCCAG | AGGAAAAGAA | AGCAAAGCG | ATTCCCGTAG | TAGCGGCGAG | 420 |
| CGAAATGGGA | GCAGCCTAAA | CCGTGAAAAC | GGGGTTGTGG | GAGAGCAATA | CAAGCGTCGT | 480 |
| GCTGCTAGGC | GAAGCAGCCC | GAATGCTGCA | CCCTAGATGG | CGAAAGTCCA | GTAGCCGAAA | 540 |
| GCATCACTAG | CTTATGCTCT | GACCCGAGTA | GCATGGGGCA | CGTGGAATCC | CGTGTGAATC | 600 |
| AGCAAGGACC | ACCTTGCAAG | GCTAAATACT | CCTGGGTGAC | CGATAGCGAA | GTAGTACCGT | 660 |
| GAGGGAAGGG | TGCCGGAATT | C | | | | 681 |

( 2 ) INFORMATION FOR SEQ ID NO:21:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:21:

CCGAGGATCC GAATTCTGTC AATCATGTCT T        31

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:22:

TGCCAAAAAG TACTTGCCAC G        21

( 2 ) INFORMATION FOR SEQ ID NO:23:

( i ) SEQUENCE CHARACTERISTICS:
        ( A ) LENGTH: 1270 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:23:

-continued

```
GAATTCTGTC AATCATGTCT TTTTTAAGAT TTGTTGGTAC AATTCTTTTC TTGGTTGCAA      60
TTTTTGCAGC ATCAAATGCT CAATTAAGCG CAACATTTTA CGATACCACT TGCCCTAATG     120
TTACAAGTAT TGTACGTGGT GTTATGGATC AAAGGCAACG TACTGATGCT CGAGCTGGTG     180
CTAAAATTAT TCGTCTTCAT TTCCATGATT GTTTGTTAA TGGTTGTGAT GGATCAATTT      240
TGTTAGACAC AGATGGGACT CAAACTGAGA AAGATGCACC TGCTAATGTA GGTGCAGGAG     300
GATTTGATAT TGTGGATGAT ATTAAAACTG CACTAGAGAA TGTATGCCCT GGTGTTGTAT     360
CTTGTGCAGA TATTTTAGCC CTTGCATCTG AAATTGGAGT TGTCTTGGCT AAAGGTCCGT     420
CGTGGCAAGT ACTTTTTGGC AGAAGAGATA GCTTAACAGC AAACCGATCT GGAGCTAATA     480
GTGATATTCC TAGCCCCTTT GAAACCCTTG CTGTAATGAC GCCACAATTC ACCAACAAGG     540
GAATGGATTT AACTGATCTT GTTGCTCTAT CTGGTGCACA CACATTTGGA AGAGCAAGAT     600
GTGGTACTTT TGAACAACGT CTCTTTAACT TCAGTGGCAG TGGTAATCCT GATCCAACCG     660
TAGACGCTAC ATTTTTACAA ACATTACAGG GAATTTGTCC TCAAGGTGGA AATAATGGCA     720
ATACTTTTAC AAATCTTGAT ATATCAACTC CTAATGATTT TGATAATGAC TATTTCACTA     780
ATCTTCAAAA TAATCAAGGA CTTCTTCAAA CTGATCAAGA GTTGTTTCT ACATCTGGAT      840
CTGCTACAAT TGCTATAGTG AATCGTTATG CTGGTAGTCA AAGTCAGTTT TTTGATGATT     900
TTATTTGCTC GATGATTAAA TTGGGTAATA TAAGTCCATT AACTGGTACT AATGGAGAGA     960
TTAGGAAAGA TTGCAAGAGG GTTAATTAAT TAATTAATTA ATTAATCAAG CAGATTATAT   1020
TAATTATCAA GATCGAGTGC TTTAATTTCT GCATGTTCTT GTGTTGTTTA ATCATGTCCT   1080
AAAGAAAGAT TGTCAGAAGT TGATGTCAT GAGTTGTAAA TTTTTTTCAT CTTTTTGACG    1140
CTTATTTTGT TTTATGTAAA TGTAATATGT GCTGAAATGG CAATTCCAAT AAGGATGTTA   1200
TGCTGAAATA GCAATTCCAA TAATTAAGGA TTTAATCCAA AAAAAAAAA AAAAAAAAA     1260
ACCGGAATTC                                                          1270
```

( 2 ) INFORMATION FOR SEQ ID NO:24:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:24:

```
GGCCAGGATC CATGTCTTTT TTAAGA                                          26
```

( 2 ) INFORMATION FOR SEQ ID NO:25:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:25:

```
TGCACCTGAT AGAGCAAC                                                   18
```

( 2 ) INFORMATION FOR SEQ ID NO:26:

( i ) SEQUENCE CHARACTERISTICS:
        ( A ) LENGTH: 31 base pairs

```
              ( B ) TYPE: nucleic acid
              ( C ) STRANDEDNESS: single
              ( D ) TOPOLOGY: linear ( i i ) MOLECULE TYPE: oligonucleotide ( x i ) SEQUENCE DESCRIPTION: SEQ ID NO:26:

CCGAGGATCC  GAATTCTGTC  AATCATGTCT  T                                            3 1

( 2 ) INFORMATION FOR SEQ ID NO:27:

( i ) SEQUENCE CHARACTERISTICS:
              ( A ) LENGTH: 21 base pairs
              ( B ) TYPE: nucleic acid
              ( C ) STRANDEDNESS: single
              ( D ) TOPOLOGY: linear ( i i ) MOLECULE TYPE: oligonucleotide ( x i ) SEQUENCE DESCRIPTION: SEQ ID NO:27:

TGCCAAAAAG  TACTTGCCAC  G                                                        2 1

( 2 ) INFORMATION FOR SEQ ID NO:28:

( i ) SEQUENCE CHARACTERISTICS:
              ( A ) LENGTH: 24 base pairs
              ( B ) TYPE: nucleic acid
              ( C ) STRANDEDNESS: single
              ( D ) TOPOLOGY: linear ( i i ) MOLECULE TYPE: oligonucleotide ( x i ) SEQUENCE DESCRIPTION: SEQ ID NO:28:

GGCCCCTTTA  AAATGCATTT  CTCT                                                     2 4

( 2 ) INFORMATION FOR SEQ ID NO:29:

( i ) SEQUENCE CHARACTERISTICS:
              ( A ) LENGTH: 24 base pairs
              ( B ) TYPE: nucleic acid
              ( C ) STRANDEDNESS: single
              ( D ) TOPOLOGY: linear ( i i ) MOLECULE TYPE: oligonucleotide ( x i ) SEQUENCE DESCRIPTION: SEQ ID NO:29:

GGTAGCCACA  TATGGCGTCG  ACTA                                                     2 4
```